US008512283B2

(12) United States Patent
Kumar et al.

(10) Patent No.: US 8,512,283 B2
(45) Date of Patent: Aug. 20, 2013

(54) TISSUE CAVITY DISTENDING SYSTEM WITH LOW TURBULENCE

(76) Inventors: Atul Kumar, Jaipur (IN); Alka Kumar, Jaipur (IN)

( * ) Notice: Subject to any disclaimer, the term of this patent is extended or adjusted under 35 U.S.C. 154(b) by 1129 days.

(21) Appl. No.: 11/211,571

(22) Filed: Aug. 26, 2005

(65) Prior Publication Data

US 2006/0122557 A1 Jun. 8, 2006

(30) Foreign Application Priority Data

Aug. 27, 2004 (IN) .............. 1619/DEL/2004

(51) Int. Cl.
*A61M 1/00* (2006.01)
*A61M 37/00* (2006.01)

(52) U.S. Cl.
USPC .................. 604/118; 604/132; 604/147

(58) Field of Classification Search
USPC ............ 607/46, 62, 115–118; 600/372, 600/373, 377, 378; 604/118, 131, 132, 147, 604/192, 190
See application file for complete search history.

(56) References Cited

U.S. PATENT DOCUMENTS

| | | | | |
|---|---|---|---|---|
| 3,811,431 A | * | 5/1974 | Apstein | 601/150 |
| 3,812,855 A | * | 5/1974 | Banko | 604/31 |
| 4,041,944 A | * | 8/1977 | Rhodes | 604/6.1 |
| 4,613,327 A | * | 9/1986 | Tegrarian et al. | 604/141 |
| 4,778,451 A | * | 10/1988 | Kamen | 604/67 |
| 5,556,378 A | | 9/1996 | Storz et al. | |
| 5,569,188 A | * | 10/1996 | Mackool | 604/67 |
| 5,605,545 A | * | 2/1997 | Nowosielski et al. | 604/118 |
| 5,630,799 A | * | 5/1997 | Beiser et al. | 604/66 |
| 5,776,104 A | * | 7/1998 | Guignard et al. | 604/132 |
| 5,814,009 A | * | 9/1998 | Wheatman | 604/21 |
| 6,319,241 B1 | * | 11/2001 | King et al. | 604/502 |
| 6,595,049 B1 | * | 7/2003 | Maginnis et al. | 73/202.5 |
| 2003/0105437 A1 | * | 6/2003 | Neubert | 604/319 |
| 2004/0073175 A1 | * | 4/2004 | Jacobson et al. | 604/251 |

FOREIGN PATENT DOCUMENTS

WO    WO 96/04029    2/1996

OTHER PUBLICATIONS

F. Loffer, et al., "Hysteroscopic Fluid Monitoring Guidelines", *Journal of the American Assoc. of Gynecologic Laparoscopists*, Nov. 10, 1999.

* cited by examiner

*Primary Examiner* — Kevin C Sirmons
*Assistant Examiner* — William Carpenter
(74) *Attorney, Agent, or Firm* — Dickstein Shapiro LLP

(57) ABSTRACT

The present invention provides a system and a method for distending a body tissue cavity of a subject by continuous flow irrigation by using a positive displacement pump, such as a pneumatic pump, on the inflow side and a positive displacement pump, such as a peristaltic pump, on the outflow side, such that the amplitude of the pressure pulsations created by a the two positive displacement pump inside the said tissue cavity is substantially dampened to almost negligible levels. The present invention also provides a method for accurately determining the rate of fluid loss, into the subject's body system, during any endoscopic procedure without utilizing any deficit weight or fluid volume calculation, the same being accomplished by using two fluid flow rate sensors. The present invention also provides a system of creating and maintaining any desired pressure in a body tissue cavity for any desired cavity outflow rate. The system and the methods of the present invention described above can be used in any endoscopic procedure requiring continuous flow irrigation few examples of such endoscopic procedures being hysteroscopic surgery, arthroscopic surgery, trans uretheral surgery, endoscopic surgery of the brain and endoscopic surgery of the spine.

30 Claims, 7 Drawing Sheets

TISSUE CAVITY DISTENDING SYSTEM WITH LOW TURBULENCE

FIELD OF INVENTION

The present invention relates to a system for distending body tissue cavities of subjects utilizing continuous flow irrigation during endoscopic procedures. The system and the methods of the present invention described above can be used in any endoscopic procedure requiring continuous flow irrigation few examples of such endoscopic procedures being hysteroscopic surgery, arthroscopic surgery, trans uretheral surgery (TURP), endoscopic surgery of the brain and endoscopic surgery of the spine. The proposed invention can also have certain useful non medical applications.

BACKGROUND OF THE INVENTION

Endoscopic surgery is becoming increasingly popular because of the following reasons:
 (a) it is a minimally invasive form of surgery,
 (b) it avoids large incisions over the skin and muscle,
 (c) it is associated with less pain,
 (d) there is a relatively less requirement of blood transfusions and
 (e) the patients can return back to normal work relatively early with minimal loss of working days.

While in the corresponding open conventional surgeries a relatively large body part consisting of skin and muscle needs to be cut in order to gain access to an underlying body tissue cavity, in endoscopic surgery instead of cutting body structures like skin and muscle an endoscope is introduced into the body cavity via the natural opening of a cavity, if such exists, or alternatively a minute hole is made in the wall of the cavity through which the endoscope is introduced to visualize the interior of the body tissue cavity and to perform major or minor endoscopic surgical procedures. For this reason endoscopic surgery is also sometimes called 'key hole' or 'minimal access surgery'. Besides reducing the pain associated with surgery, endoscopic surgery also helps in reducing the medical expenses.

Endoscopic Surgery is Primarily Related to a Tissue Cavity:
 All endoscopic surgeries are carried out on a existing body cavity which is distended or 'ballooned up' by a suitable distending apparatus which permits the inner lining of the said tissue cavity to be visualized by the help of an endoscope. Though multiple endoscopic procedures have become established as the preferred surgical modality but still there is immense scope of increasing the safety and efficiency of the such existing endoscopic procedures by improving upon the existing techniques and apparatus used for distending body tissue cavities. Hysteroscopy, arthroscopy, TURP (transuretheral resection of the prostate), endoscopic surgery of the brain and endoscopic surgery of the spine are few of the routinely performed endoscopic procedures and the organs related to such surgeries being uterus, human joints, bladder, brain and the spine respectively. The list of endoscopic surgeries is long, ever increasing and there is hardly any body organ or organ system to which the benefits of endoscopy have not been extended.

Tissue Cavity is Initially Collapsed in its Natural State:
 In the natural state tissue cavities are collapsed structures and the cavity walls are in apposition with each other as if kissing each other. Thus if an endoscope is introduced in such a collapsed cavity no endoscopic visualization is possible unless the cavity is ballooned up by filling it with a transparent fluid or a gas. Such ballooning of a tissue cavity is technically termed as 'cavity distension'. No endoscopic procedure can be performed without an efficient cavity distending system and no endoscopic procedure should be attempted without a safe distending system because unsafe tissue cavity distending means can lead to extreme human morbidity and even the death of a patient and such grim realities shall be discussed in the later sections of this manuscript Cavity distension provides both endoscopic visualization and mechanical distension which is necessary for the movement of endoscopic instruments.

Continuous Flow Irrigation:
 In the present invention, the Inventors are focused on a system for distending body tissue cavities for those endoscopic procedures in which the cavity needs to be distended by utilizing continuous flow irrigation only. Here, the term 'continuous flow irrigation' means that fluid simultaneously enters and escapes from a tissue cavity via separate entry and exit points, as a result of which a positive fluid pressure is created inside the tissue cavity which distends the cavity.

The Need for Continuous Flow Irrigation:
 Any tissue cavity can be easily distended in a 'static manner' by simply pushing fluid via a single inflow tube inserted into the cavity and in this manner a desired cavity pressure can be developed and also maintained. For example, a cavity can be distended by pressing on the piston of a simple syringe filled with fluid with the outlet end of the syringe being connected to the cavity by a tube. Alternatively a fluid filled bottle may be elevated to a suitable height and under the influence of gravity fluid from such bottle may be allowed to enter the cavity via a tube connecting the said bottle to the cavity and in this manner a desired static pressure can be developed and also maintained. Though it is very easy to achieve distension by the said static manner, it is not a practical solution because blood and tissue debris which are invariably released from the fragile cavity inner lining mix with the distending fluid and endoscopic vision gets clouded within a few seconds or a few minutes. Thus continuous flow irrigation is needed to constantly wash away blood and tissue debris in order to maintain constant clear endoscopic vision.

Cavity Pressure and Cavity Flow Rate:
 It is obvious that cavity fluid pressure and the flow rate through the cavity are the two basic parameters associated with all continuous flow irrigation systems.

An Efficient Distending System:
 The Inventors believe that an efficient distending system is the one which provides a predictably continuous clear visualization and a predictably stable mechanical stabilization of the cavity walls. In order to achieve this the Inventors believe that a suitable stable constant precise cavity pressure and a suitable stable precise cavity flow rate have to be created and maintained in a predictable and controlled manner. The cavity pressure should be adequate so that vision is not clouded by oozing of blood and enough mechanical separation of the cavity walls occurs to allow the movement of the endoscope. Similarly, the cavity flow rate should be adequate enough to constantly wash away blood and tissue debris in order to allow clear vision. Many prior systems utilize a peristaltic pump over the inflow and or the outflow side and these peristaltic pumps create pressure pulsations which are then transmitted to the tissue cavity. Such pressure pulsations are undesirable and the main aim of the present invention is to dampen such pressure pulsations.

A Safe Distending System:
 An efficient distending system as explained in the previous paragraph need not also be a safe distending system. In this regard, the Inventors would like to highlight that if the cavity pressure rises above the prescribed safe limits excessive fluid intravasation may occur or the cavity may even burst. Fluid intravasation is a process by which the irrigation fluid enters into the patient's body system through the cavity walls and may cause significant danger to the patient's life including death. Thus a safe distending system is one which prevents or minimizes fluid intravasation and allows the surgeon to accurately know the instantaneous real time rate of fluid intravasation into the patient's body system.

No Prior Art is Absolutely Safe:

Many different types of uterine distending systems are known and are being commercially marketed by many different companies but none of these systems can be considered to be absolutely safe for the patient. This fact has been clearly stated in the 'Hysteroscopic, Fluid Monitoring Guidelines proposed by the Ad Hoc Committee on Hysteroscopic Fluid Guidelines of the American Association of Gynecologic Laproscopists February 2000 (Loffler F D, Bradley L D, Brill A I et al: Hysteroscopic fluid monitoring guidelines. The journal of the Americal Association of Gynecologic Laproscopists 7 (1): 167-168, 1994) where the authors clearly and explicitly state "fluid pumps for low-viscosity media are a convenience and do not guarantee safety". The present invention aims at providing a distending system which is both safer and more efficient in comparison to all the prior art systems.

Basic Physics of Cavity Distension:

Although, a person skilled in the art may know it, the Inventors would like to provide a brief description of the basic physics of cavity distension. Filling the tissue cavity with fluid enables distension of the same. Initially more fluid is pumped in than the amount which is extracted from the cavity and ultimately the inflow rate is fixed at a level where a somewhat desired cavity pressure and distension is achieved. It may be possible to accurately maintain the desired pressure and distension in the case of a rigid cavity, for example a cavity made of steel.

However, the body tissue cavities are not rigid because they are distensible and also have some element of elasticity. Thus a distended tissue cavity in its attempt to constantly revert back to its natural collapsed state reacts by exhibiting physiological contractions of the cavity wall which generally leads to variations in the cavity pressure which ultimately culminates in irregular movement excursions of the cavity walls. In a static system the said movement excursions may be so minute that they may even go unnoticed. However in a dynamic system such that being created during an endoscopic procedure, the said physiological cavity wall contractions may cause the cavity to expel out its entire fluid content thus leading to a surgically dangerous large magnitude movement excursion of the cavity wall. Because of these reasons it is extremely difficult to maintain the cavity pressure and cavity distension in a predictably stable fashion.

Further, the inflow tube, the out flow tube and the endoscope also invariably move and shake during surgery which leads to variations in fluid flow resistance which is also manifested in the form of variations in the cavity pressure. The cavity pressure variations occurring as a result of cavity wall contractions and the mechanical movement of the tubes and the endoscope tend to occur again even if they are corrected once because it is impossible to prevent the physiological cavity wall contractions and the mechanical movements of the irrigation circuit. Thus, the said cavity pressure variations shall continue to occur even after multiple repeated corrections.

Thus, till date the surgeon was only left with two options, either to ignore the said cavity pressure variations by not correcting them, or to externally and actively correct such pressure variations. The Inventors have noticed that any attempt to externally and actively correct the said cavity pressure variations leads to an undesirable turbulence inside the cavity and also tends to amplify the resultant movement excursions of the cavity walls. Thus there is a grave need to provide a system which can maintain an almost constant and stable cavity pressure even in the presence of the said physiological cavity contractions and the mechanical movements in the irrigation circuit.

Brief Description of an Endoscope:

Prior to describing the basic layout of a continuous flow irrigation system the basic structure of an 'endoscope' needs to be described. Endoscope is a cylindrical tube having an outer diameter ranging between 3 to 9 mm approximately. A typical endoscope has four channels. One channel is meant to pass a fibereoptic telescope while endoscopic instruments are negotiated through a second instrument channel. A third channel also known as the inflow channel is used for pushing irrigation fluid into a tissue cavity, the proximal end of this channel ending in a metal adaptor known as the inflow port while the distal end of this inflow channel opens near the tip of the endoscope. The inflow port is connectable to an inflow tube which carries sterile irrigation fluid from a fluid source reservoir. A fourth channel also known as the out flow channel is meant for extracting waste fluid out of the cavity, the proximal end of this channel ending in a metal adaptor known as the outflow port while the distal end of this outflow channel opens near the tip of the endoscope. The outflow port is connectable with an outflow tube which transports the waste fluid from the cavity to a suitable waste fluid collecting reservoir. A set of fiber optic bundles contained inside the telescope transmit light energy produced by an external light source. This light energy illuminates the walls of the tissue cavity. The image thus formed is carried via a separate set of optical pathways again situated inside the telescope. A video camera attached to the eye piece of the telescope forms a clear endoscopic image of the cavity on a TV monitor. The endoscopic surgeon has to continuously look at the TV monitor all through the endoscopic procedure.

Basic Layout of a 'Continuous Flow Irrigation System:

Henceforth in this manuscript unless otherwise specified the term 'distension' shall be deemed to imply tissue cavity distension by 'continuous flow irrigation' only and the term 'cavity' unless specifically stated shall be deemed to refer to a 'body tissue cavity'. In a typical distension system a physiological non viscous liquid like 0.9% normal saline, 1.5% glycine, mannitol, ringer's lactate and 5% dextrose is stored in a sterile fluid source reservoir. A fluid supply tube connects the said fluid reservoir with the inlet end of a pump. The outlet end of the inflow pump is connected to the inflow port of an endoscope. When the inflow pump operates the fluid from the fluid source reservoir is sucked via the fluid supply tube and the inflow pump pushes this fluid into the tissue cavity via the said inflow tube. The pump operates by consuming certain amount of energy and as a result of this a positive fluid pressure is created inside the tissue cavity. An outflow tube extends between the outflow port and the inlet end of an outflow pump. When the outflow pump operates it actively extracts waste fluid from the cavity again at the expense of energy and this waste fluid is ultimately sent to a waste fluid reservoir via a tube which connects the outlet end of the outflow pump with the waste fluid reservoir. Alternatively the outflow pump may be missing and in such case the outflow tube directly carries the waste fluid from the cavity to the waste fluid reservoir and the energy for such act is supplied by gravity instead of the outflow pump. Also, the inflow pump may be missing and in such case the inflow tube directly supplies the irrigation fluid from a fluid source reservoir to the cavity. In such case the fluid source reservoir is hung at a suitable height above the patient and the said energy for cavity distension is derived from gravity instead of the inflow pump. A suitable pressure transducer is attached to the inflow tube, the outflow tube or directly to the cavity to measure the fluid pressure. A controller may be incorporated to regulate the system.

The Simplest Continuous Flow Irrigation System:

In its simplest form, a continuous flow irrigation system comprises a fluid reservoir bottle hung at a suitable height above the patient and an inflow tube connecting this fluid reservoir to a tissue cavity. An out flow tube is incorporated to remove fluid from the tissue cavity. In this system there is no pump and no transducer. In such a system fluid flows from the fluid source reservoir into the cavity and the required energy is supplied by gravity. The pressure developed inside the cavity can be increased or decreased by elevating or lowering the height of the fluid source reservoir. In such system the main limiting factor is the height of the room ceiling beyond which the fluid reservoir cannot be raised. This is a crude system having negligible practical importance and has been included only from the academic point of view. Also in such a system unlimited volume of irrigation fluid may enter into the patient's blood circulation. Thus such system is not suitable even from the patient safety point of view.

Basic Components of a Continuous Flow Irrigation System:

Like a motor car is made up of certain obvious components like engine, tyres and a steering wheel, a continuous flow distending system is made of components like pump, pressure transducer, flow regulating valve, rubber tubes and a controller. The pump may be a positive displacement pump like a peristaltic pump, piston pump or a gear pump or alternatively it may be a dynamic pump like a centrifugal pump. Further the said pump may be of a fixed RPM type which runs at fixed RPM all through the endoscopic procedure or the pump may be of a variable RPM type which operates at variable RPM during the endoscopic procedure. It is extremely important to note that fixed RPM pumps and variable RPM pumps are two separate mechanical entities in context with a cavity distending system because the fixed and variable RPM pumps impart different surgical efficiency and patient safety criteria to the distending system. The said pump may be attached on the inflow side only, on the outflow side only or both on the inflow and outflow side. Further if a pump is attached only on the inflow side the outflow tube may directly empty in a waste fluid reservoir at atmospheric pressure or a vacuum source may also be additionally attached. In some distending systems a flow controlling valve is attached on the outflow tube in order to regulate the cavity pressure. There may be a single pressure transducer attached to the inflow tube, the outflow tube or directly to the cavity. In some systems instead of one pressure transducer two pressure transducers may be used, one on the inflow tube and the other on the outflow tube.

Description of a Prior Art System Using a Pneumatic Pump on the Inflow Side

This type of system has been described in U.S. Pat. No. 5,814,009 (Wheatman). This patent is related to product Dolphin II Fluid Management System marketed by ACMI CIRCON. In this system the irrigation fluid is pushed into the uterine cavity by the help of a bladder pump which compresses the irrigation fluid contained in a collapsible plastic container. The outflow tube opens directly into a waste fluid collecting container at atmospheric or in a waste fluid collecting container having a vacuum source attached to it. In this system a pressure transducer located in the downstream portion of the inflow tube near the inflow port constantly senses the cavity pressure and sends appropriate signals to a controller which by a feedback mechanism regulates the air pressure inside the bladder enclosing the said collapsible fluid source container. If the said pressure transducer senses a fall in the tissue cavity pressure it sends a feedback signal to the said controller via a feedback mechanism and the controller in turn increases the air pressure inside the said bladder by activating an air compressor which results in the collapsible fluid source container being compressed with a greater force which culminates in an increased inflow rate and the end result being an increased uterine cavity pressure. Similarly when the uterine cavity pressure increases the controller causes the bladder pressure to decrease and the end result being a reduced uterine cavity pressure. In this system the cavity pressure is maintained by irregularly fluctuating around a preset value, thus implying that in the said system the pressure cannot be maintained at a fixed and precise value. The differences between this system related to U.S. Pat. No. 5,814,009 and the system of the proposed invention are given below in table 1.

Table 1: Comparison of the System of Wheatman et al (U.S. Pat. No. 5,814,009) with the system of the proposed invention

| THE PROPOSED INVENTION | U.S. Pat. No. 5814009 (Wheatman) |
|---|---|
| The inflow pneumatic pump operates at a fixed flow rate. | The inflow pneumatic pump operates at a variable flow rate. |
| A positive displacement pump is present on the outflow side. | No pump is present on the outflow side. |
| It being possible to create and maintain any desired precise cavity pressure for any desired precise constant tissue cavity outflow rate, for any length of time. | Not possible. |
| It is possible to reduce the amplitude of the pressure pulsations created by the inflow pneumatic pump to almost negligible magnitude irrespective of the pump RPM. | Not possible. |
| It is possible to reduce the amplitude of the pressure pulsations created by the outflow peristaltic pump to almost negligible magnitude irrespective of the pump RPM. | No pump has been provided on outflow side. |
| It is possible to minimize cavity fluid turbulence to almost negligible levels. | This is not possible in any prior art system. |
| It being possible to maintain the cavity pressure at any desired precise value for any length of time. | No, the cavity pressure continuously fluctuates around a preset value. |
| It being possible to know the instantaneous real time rate of fluid intravasation by using two fluid flow rate sensors. | This feature is not present. |
| It being possible to maintain any desired high cavity pressure without increasing the 'maximum possible intravasation rate'. | Not possible. |
| It being possible to predictably maintain a constant clear visualization and a stable cavity distension for any length of time. | Not possible. |
| It is possible to achieve a predictably stable mechanical distension of the cavity walls. | Not possible. |

Relvant references have been included in a PCT application filed by the Inventors in the past numbered PCT/IB/002341 and the same may also be deemed to have been included in the present application. In addition, three references U.S. Pat. Nos. 5,520,638, 4,902,277 and 5,578,012 are now being included and discussed herebelow.

In the U.S. Pat. No. 5,520,638 a variable speed peristaltic pump is used to push irrigation fluid into a tissue cavity. This patent is related to the 'Continuous Wave II Arthroscopy Pump' marketed by Arthrex. A chamber with volume is connected to the inflow tube and a collapsible bladder is contained within the bladder. The collapsible bladder has an open end connected with tubing to a pressure transducer. Once activated the pump begins to introduce fluid into the tissue cavity via the inflow tube and as pressure builds within the tissue cavity, fluid enters the chamber, and air in the chamber is compressed. The compressed air in the chamber compresses the bladder. Air pressure in the bladder is experienced by the pressure transducer. The pressure transducer feeds pressure information to a controller which regulates the RPM of the pump on the basis of a pressure feedback mechanism. Thus by the help of a pressure feedback mechanism the pressure inside a tissue cavity is maintained by fluctuating around a desired value. In this invention an important purpose of the said chamber is to dampen the pressure pulsations created by the peristaltic pump. Such pressure pulsations create turbulence inside the tissues cavity and are hence undesirable. The method of dampening the pressure pulsations as described in this U.S. Pat. No. 5,520,638 is not adequately efficient, especially at high pump RPM's. The Inventors would like to submit that the system being claimed in the aforesaid US Patent is a passive dampening system. The system is only able to passively correct the small pressure pulsations. In the present invention a method shall be described by which the amplitude of the said pressure pulsations would be reduced to negligible magnitude even at a high pump RPM.

In U.S. Pat. No 4,902,277 a pump is provided on the inflow side which pushes fluid into a tissue cavity while a positive displacement pump removes fluid from the cavity. This patent is related to 'FMS duo Fluid Management System' marketed by FMS Group. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

In U.S. Pat. No. 5,578,012 a centrifugal pump is deployed on the inflow side while no pump is deployed over the outflow side. This patent is related to the 'HydroFlex HD' pump marketed by DAVOL company. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

Inventors own PCT Application No. PCT/IB04/002341 filed on 21 Jul. 2004 and the contents of the same may also deemed to be included in the present application and could be referred to as and when found necessary.

OBJECTS OF THE INVENTION

The overall objective of the invention is to provide a safe, efficient and turbulence free system for distending body tissue cavities for those endoscopic procedures which utilize continuous flow irrigation.

The main object of the invention is to minimize the amplitude as well as the frequency of pressure pulsations, inside the tissue cavity, created by the two positive displacement pumps. Another object of the present invention is to provide a system for distending tissue cavities using which it being possible to create and maintain a desired precise cavity pressure for a desired precise rate at which fluid may be allowed to flow through the cavity, for any length of time.

Still another object of the present invention is to provide a system for distending tissue cavities using which it being possible to achieve a predictably constant clear endoscopic vision throughout the endoscopic procedure.

Yet another object of the present invention is to provide a system for distending tissue cavities using which it being possible to achieve predictably stable mechanical cavity distension throughout the endoscopic procedure.

One more object of the present invention is to provide a system for distending tissue cavities using which it being possible to predictably maintain the cavity pressure at any desired precise value despite physiological contractions of the cavity wall.

One another object of the present invention is to provide a system for distending tissue cavities using which it being possible to constantly, accurately and reliably determine the instantaneous real time rate of fluid intravasation into the patient's body by using two fluid flow rate sensors which do not have any movable components.

A further more object of the present invention is to provide a system for distending tissue cavities using which it being possible to maintain any desired precise and high cavity pressure without increasing the 'maximum possible fluid intravasation rate'.

Another object of the present invention is to provide a system for distending tissue cavities using which it being possible to measure the actual cavity pressure, in an accurate, reliable and simple manner, by using a pressure transducer located far away from the cavity in the up stream portion of the inflow tube.

Yet another object of the present invention is to provide a system for distending tissue cavities using which it being possible to make the pressure inside the body cavity and the flow rate of the fluid passing through the body cavity absolutely independent of each other such that the value of any may be altered without affecting the value of the other.

Still another object of the present invention is to provide a system for distending tissue cavities using which it being possible to reduce the cavity filling time in a predictably controlled manner and at the same time achieving a desired cavity pressure at the end of the cavity refilling phase, cavity refilling time being the time taken to completely fill a cavity with the irrigation fluid.

One more object of the present invention is to provide a system for distending tissue cavities using which it being possible for the surgeon to have a fairly accurate assessment of the total volume of the irrigation fluid which would be required to complete the entire endoscopic procedure.

On another object of the present invention is to provide a system for distending tissue cavities using which it being possible for the surgeon to accurately know the maximum pressure which develop inside the cavity in case of an accidental obstruction of the outflow tube and it should be possible to minimize such rise in the cavity pressure in a controlled and predictable manner.

SUMMARY OF THE INVENTION

The present invention provides a safe and an efficient system for distending body tissue cavities for those endoscopic procedures which utilize continuous flow irrigation. The main aim of the invention is to minimize cavity fluid turbulence by minimizing the amplitude as well as the frequency of the pressure pulsations in a tissue cavity created by two positive displacement pumps. The present invention is a system of creating and maintaining a desired positive pressure inside a body tissue cavity through which fluid is made to flow at a desired flow rate. Alternatively the present invention may be considered as a system of creating cavity fluid pressure which is absolutely independent of the cavity outflow rate. The present invention comprises of two positive displacement pumps which work simultaneously, for indefinite time, at fixed flow rates to create and maintain any precise desired cavity pressure for any desired cavity outflow rate, including a zero outflow rate. The present invention comprises of a dynamic pump like a pneumatic piston pump on the inflow side and a positive displacement pump such as a peristaltic on the outflow side which work simultaneously, for indefinite time, at fixed RPM's to create and maintain a desired precise cavity pressure for a desired cavity outflow rate. In the present invention the amplitude of tissue cavity pressure fluctuations caused by two positive displacement outflow and inflow pumps can be minimized to almost negligible levels. Also in the proposed invention the changes in the tissue cavity pressure is not actively corrected as is done in the prior art systems. Further if any fluid is being absorbed into or through the cavity walls, such as fluid intravasation which occurs during hysteroscopic endometrial resection, the instantaneous real time rate of such fluid absorption can be constantly determined by utilizing two fluid flow rate sensors. Also the cavity pressure can be maintained at any desired high value without increasing the 'maximum possible fluid intravasation rate'. In the proposed invention by synchronizing the inflow and the outflow pumps it is possible to reduce fluid turbulence to almost negligible levels. The proposed invention also has multiple other features of endoscopic surgical relevance which greatly enhance the patient safety and efficiency during endoscopic surgery few such features being shortening of the cavity refilling time in a predictably controlled fashion, to be able to predict by a fair degree of accuracy the volume of fluid which would be required to complete the endoscopic procedure, to be able to predict and limit the magnitude of the maximum increase in the cavity pressure or the magnitude of a minor pressure surge which might occur in case of an accidental obstruction of the outflow tube for a specific outflow rate. Also the same system can be used for all types of endoscopic procedures which utilize continuous flow irrigation.

DETAILED DESCRIPTION OF INVENTION

Figure 1:
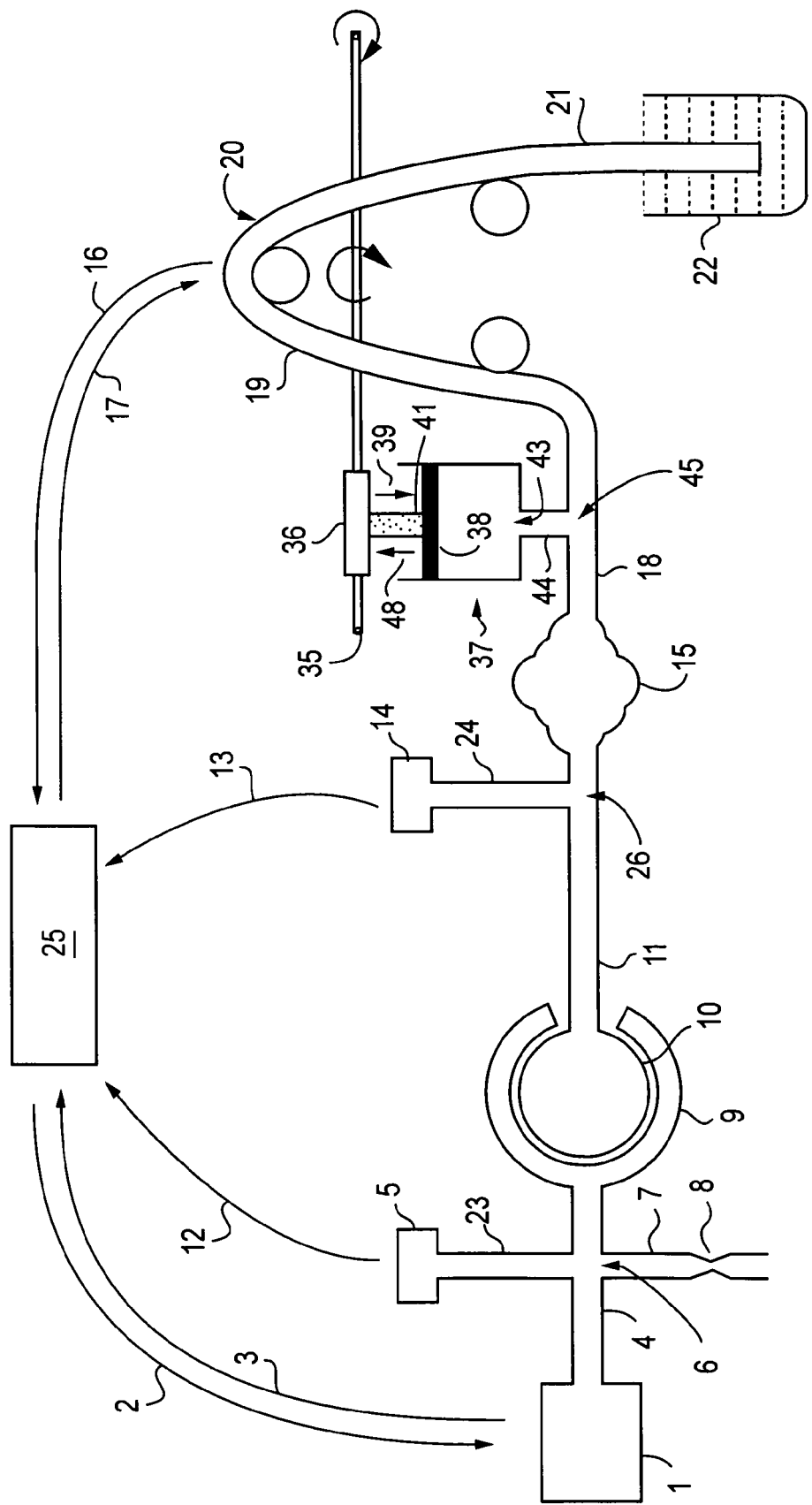
FIG. 1 shows the main invention with a pressure pulse dampening system.

Accordingly, the present invention provides a system for distending body tissue cavities of subjects by continuous flow irrigation during endoscopic procedures the said system comprising:

a collapsible fluid source reservoir containing a non viscous physiologic fluid meant for tissue cavity distension;

said fluid source reservoir being encircled by a bladder cavity, said bladder cavity being connected to an inflow positive displacement pump through an air transporting tube for inflating the same and a pressure transducer being coupled to the air transporting tube;

a fluid supply inflow tube connecting the fluid source reservoir to an inflow port of an endoscope instrument for pumping the fluid at a controlled flow rate into the body tissue cavity, the flow rate of the said inflow pump being termed as the inflow rate and the rate at which the fluid from the inflow tube enters into the tissue cavity being termed as the cavity inflow rate;

an inflow liquid pressure transducer being coupled to the fluid supply conduit tube;

an outflow port of the endoscope being connectable to an inlet end of a variable speed positive displacement outflow pump through a outflow tube for removing the fluid from the cavity at a controlled flow rate, the flow rate of the said outflow pump being termed as the cavity outflow rate, an outlet end of the outflow pump being connected to a waste fluid collecting container via a waste fluid carrying tube, and characterized that a housing tube having a controllable constriction site is being coupled to the air transporting tube between the positive displacement inflow pump and the bladder cavity; wherein the housing tube provides a route for any excess air present in the bladder cavity or being pumped by the positive displacement pump to escape to the atmosphere, thereby minimizing turbulence inside the body tissue cavity and maintaining the body tissue cavity pressure at a stable value despite physiological contractions of the body tissue cavity wall.

In an embodiment of the present invention, a proximal end of the fluid supply conduit tube is connected to the fluid source reservoir and a distal end of the tube being connectable to the inflow port of the endoscope instrument.

In another embodiment of the present invention, the positive displacement inflow pump is a piston pump.

In yet another embodiment of the present invention, the housing tube is releasably provided between the positive displacement pump and the bladder cavity to enable replacement of the housing tube with yet another housing tube having a different diameter at the constriction site to suit the operational need of the endoscopic procedure.

In still another embodiment of the present invention, the housing tube is provided with a clamping means at the constriction site to enable the user to vary the diameter of the housing tube at the constriction site to suit the operational needs of endoscopic procedures.

In one more embodiment of the present invention, the diameter of the housing tube at the constriction site is in the range of 0.001 mm to a maximum value which is less than the overall diameter of the rest of the housing tube.

In one another embodiment of the present invention, the diameter of the housing tube at the constriction site is in the range of 0.01 to 2.5 mm.

In a further embodiment of the present invention, the inflow pressure transducer is located sufficiently away from the cavity site, preferably near the outlet end of the inflow pump from the practical point of view, such that the fluid pressure measured by the same is almost equal to the fluid pressure inside the cavity.

In a further more embodiment of the present invention, a proximal end of the outflow tube being connectable to the outlet port of the endoscope instrument and a distal end of the outflow tube is connected to an inlet end of the variable speed positive displacement outflow pump.

In another embodiment, the system of the present invention further comprises an inflow gas pressure transducer connected between the positive displacement pump and the bladder cavity.

In yet another embodiment, the system of the present invention further comprises an outflow pressure transducer connected between a proximal end of the outflow tube and the inlet end of the variable speed positive displacement outflow pump for measuring the pressure in the outflow tube.

In still another embodiment of the present invention, the variable speed positive displacement outflow pump is selected from the group comprising peristaltic pump, piston pump, gear pump, diaphragm pump and plunger pump.

In one more embodiment of the present invention, the variable speed positive displacement outflow pump is a peristaltic pump.

In one another embodiment of the present invention, the outlet end of the variable speed positive displacement outflow pump is connected to the waste fluid collecting container through a waste fluid carrying tube.

In yet another embodiment, the system of the present invention further comprises a micro-controller means electrically coupled to the inflow gas pressure transducer, the inflow liquid pressure transducer, the outflow pressure transducer, the inflow positive displacement pump and the outflow pump for regulating the operation of the inflow and the outflow pumps.

In still another embodiment of the present invention, the housing tube is provided with an electromechanical device, a solenoid, to enable the micro-controller to vary the diameter of the constriction site.

In one more embodiment, the system of the present invention further comprises a housing tube having a variable size constriction site being provided between the outflow tube and the waste fluid reservoir.

In one another embodiment of the present invention, a proximal end of the housing tube is connected to the outflow near the inlet of the outflow pump.

In an embodiment, the system of the present invention further comprises a fluid replenishing tube connected either directly or indirectly to the fluid source reservoir through a replenishment fluid controlling valve for refilling the fluid source reservoir.

In another embodiment of the present invention, the fluid replenishing tube is connected directly to the fluid source reservoir or via the fluid supply inflow tube to the fluid source reservoir.

In yet another embodiment of the present invention, an inflow fluid controlling valve is provided on the inflow tube for preventing the fluid from entering into the tissue cavity during fluid replenishment phase.

In still another embodiment of the present invention, the fluid supply conduit tube and the outflow tube and the waste fluid carrying tube are flexible, disposable and are made of polymeric material.

In one more embodiment, the system of the present invention further comprises a fluid inflow rate sensor connected to the inflow tube.

In one another embodiment of the present invention, the fluid inflow rate sensor is located in the lumen or wall of the inflow fluid supply conduit tube for measuring the cavity inflow rate. In another embodiment, the system of the present invention further comprises a fluid outflow rate sensor connected between the proximal end of the outflow tube and the inlet end of the variable speed positive displacement outflow pump for measuring the cavity outflow rate.

In yet another embodiment of the present invention, the fluid inflow and the outflow rate sensors consist of a heating coil in physical contact with a metal plate for heating the same and a temperature sensor placed in contact with the metal plate for measuring the temperature of the said metal plate, the temperature of the metal plate being a function of the fluid flow rate.

In still another embodiment of the present invention, the fluid rate flow sensor is a hot wire anemometer.

In one more embodiment of the present invention, instantaneous real time rate of fluid intravasation is determined by electrically connecting the inflow and outflow fluid flow rate sensors to a micro-controller.

In one another embodiment, the system of the present invention further comprises an inflow pressure variation dampening means provided on the inflow side for dampening the pressure variation inside the body tissue cavity caused by the positive displacement inflow pump.

In one further embodiment of the present invention, the inflow pressure variation dampening means comprises a single outlet syringe mechanism, the piston of the same being coupled synchronously to the positive displacement inflow pump through a coupling means and the single outlet end of the said syringe mechanism being connected to the air transporting tube.

In another embodiment, the system of the present invention further comprises an outflow pressure variation dampening means provided on the outflow side for dampening the pressure variation inside the body tissue cavity caused by the positive displacement outflow pump.

In yet another embodiment of the present invention, the outflow pressure variation dampening means comprises a single outlet syringe mechanism, the piston of the same being coupled synchronously to the positive displacement outflow pump through a coupling means and the single outlet end of the said syringe mechanism being connected to the outflow tube.

The present invention also provides a method of distending a body tissue cavity of a subject by continuous flow irrigation such that minimal or negligible fluid turbulence is present inside the cavity, such that any desired cavity pressure can be created and maintained for any desired outflow rate, said method comprising the steps of:

(a) inflating a bladder cavity that encircles a collapsible fluid source reservoir using a positive displacement pump for dispensing a non viscous physiologic fluid meant for cavity distension from the fluid source reservoir to an inflow port of an endoscope instrument at a controlled flow rate through one or more fluid supply conduit tubes;

(b) injecting the non-viscous physiologic fluid at a controlled flow rate into the cavity for distending the body tissue cavity of the subject, the rate at which the fluid enters into the tissue cavity from via the inflow fluid conduit being termed as the cavity inflow rate;

(c) removing a waste fluid from the cavity via the outlet port of the endoscope;

(d) actively extracting the waste fluid via the outlet port of the endoscope and transporting it to a waste fluid collecting reservoir at a controlled flow rate, the said flow rate being termed as the cavity outflow rate, through a outflow conduit tube, a variable speed positive displacement outflow pump and a waste fluid carrying tube and (e) providing a housing tube having a controllable constriction site between the bladder cavity and the positive displacement inflow pump such that the housing tube provides a route for any excess air being pumped by the positive displacement pump or due to the physiologic contraction of the body tissue cavity walls escape to the atmosphere, thereby avoiding turbulence inside the body tissue cavity and to maintain a stable pressure inside the body tissue cavity.

The proposed invention is described hereafter with reference to the accompanying drawings in order to clearly explain and illustrate the system and the working of the system. It is respectfully submitted the scope of the invention should not be limited by the description being provided hereafter.

The system of the present invention is a unique system for distending body tissue cavities in endoscopic procedures. In the proposed invention a body tissue cavity is distended by continuous flow irrigation in such a manner that the amplitude of the pressure pulsations created by a positive displacement outflow pump and a positive displacement, inflow pneumatic piston pump, can be reduced to a negligible value. In the proposed invention a method of reducing of the said pulsations has been described. Also the cavity pressure is absolutely independent of the cavity outflow rate, such the both, the cavity pressure and the outflow rate, may be independently altered without varying the value of the other parameter. FIG. 1 shows the main diagram of the invention. In FIG. 1 an outflow 'pressure pulse dampening system', has been shown clearly. However in order understand the invention in a simpler manner, first the basic invention without the said 'pressure pulse dampening system' shall be discussed by taking the help of FIGS. 2 and 3. FIG. 3 is similar to FIG. 2 except that in FIG. 3 a controller 25 in not included, and the said 'pressure pulse dampening system' is also not shown in FIGS. 2 and 3 as already stated. The two pumps 3 and 20 operate simultaneously in order to distend a tissue cavity in such a manner that the cavity pressure is totally independent of the cavity outflow rate.

Figure 2:
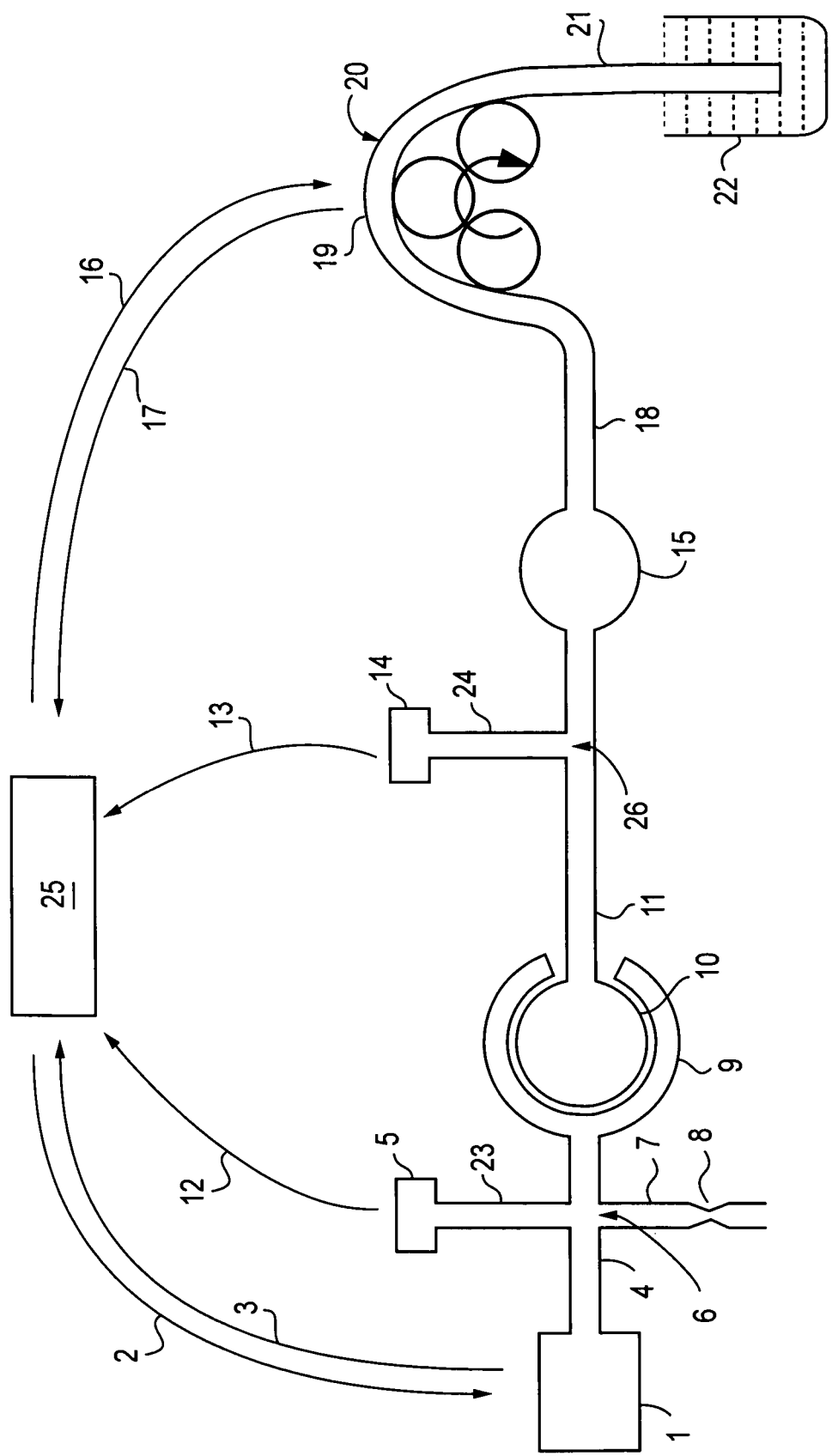
FIG. 2 is similar to FIG. 1 except that the pressure pulse dampening system has not been included.
Figure 3:
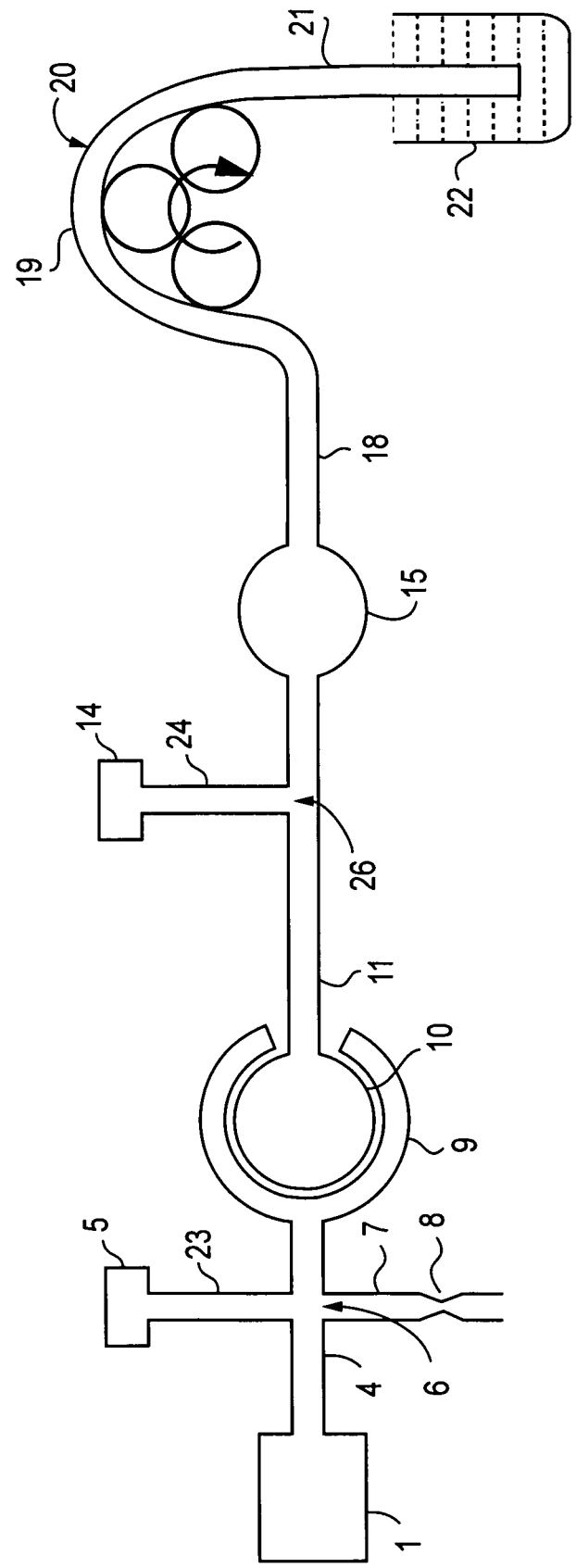
FIG. 3 is similar to FIG. 2 except that the controller has not been included.

Referring to FIG. 2 a positive displacement pump, preferably a piston pump 1 is used to for instilling air into a bladder cavity 9. This pump in the form of a piston pump 1 installed on the inflow side of the irrigation circuit shall be termed as 'pneumatic pump' in the rest of the manuscript. The pump 1 shall also be referred to as the 'inflow pump' as it is located on the inflow side of the irrigation circuit. A positive displacement pump, preferably a peristaltic pump 20 is attached on the outflow side of the irrigation circuit. The two pumps 1 and 20 can operate simultaneously in order to distend a tissue cavity in such a manner that the cavity pressure is totally independent of the cavity outflow rate. Please note that the controller being used in the system shown in FIG. 1 is an optional feature and the system would provide most of the features even without the controller. The FIG. 3 represents the schematic diagram of the invention but without a controller system. Thus FIG. 3 is a mechanical version of the invention. A human operator is required to operate such mechanical version of the invention shown in FIG. 3. Though it is recommended that the controller based version of the invention be used in endoscopic surgeries, it is not essential. The controller being used in the present invention merely assists the user in arriving easily at some of the additional functions which otherwise can be performed manually. Thus, in this manuscript the mechanical version of the invention shown in FIG. 3 is being discussed in more detail in order to explain the basic physical principals of the invention with a greater clarity.

Referring to FIG. 3, the system shown in this figure comprises of a pneumatic pump and a peristaltic pump which can maintain a predictably precise stable cavity pressure for indefinite time by working simultaneously at fixed RPM's. Pneumatic pump 1 pushes air into a bladder cavity 9 which encloses a suitable collapsible plastic fluid source container 10 which contains sterile non viscous physiological fluid like 0.9% normal saline, 1.5% glycine, ringer lactate or 5% dextrose fluid. When the pneumatic pump 1 operates air flows into the bladder, cavity 9 via a air transporting tube 4 which creates a positive pressure inside the bladder cavity 9 which compresses the fluid contained in the fluid source container 10 which causes the pressurized irrigation fluid to be expelled out of the fluid source container 10 and this irrigation fluid flows into the tissue cavity 15 via an inflow tube 11. The out flow peristaltic pump 20 simultaneously extracts fluid out of the tissue cavity 15 via an out flow tube 18. A constriction site housing tube 7 is attached anywhere to the air transporting tube 4, such as at a point 6. The said constriction site housing tube 7 has a constriction point 8 which can be located anywhere along its length. Such constriction point refers to a point where the inner diameter of the lumen of tube 7 is reduced in comparison to the lumen of the rest of the tube 7. One end of tube 7 is connected to the air transporting tube 4 while the other end just opens into the atmosphere. Such constriction may be a permanent constriction in the lumen of tube 7 or it may be a variable constriction whose diameter may be increased or decreased as desired. A suitable pressure transducer 5 connected anywhere to the air transporting tube 4 via a tube 23, such as at point 6, measures the air pressure in the bladder cavity 9. The bladder cavity 9 is assumed to be absolutely distensible but not elastic. A pressure transducer 14 is attached at one of tube 24 while the other end of tube 24 is connected anywhere on inflow tube 11. For practical convenience it is desirable that the said other end of tube 24 be connected in the up stream part of the inflow tube 11 such as at point 26. For practical convenience the point 26 may be located in the pump housing itself. The pressure transducer 14 measures the fluid pressure via a column of liquid or air present in the lumen of tube 24. The fluid pressure as measured by the pressure transducer 14 shall be referred to as P. In this manuscript the term 'P' shall frequently be used to refer to the actual pressure inside the tissue cavity but in physical terms P is the pressure sensed by the transducer 14 at point 26. The pressure transducer 14 may also be in the form of a membrane diaphragm incorporated in the wall of the inflow tube 11 such that this membrane diaphragm is in direct contact with the fluid contained in the inflow tube 11, such that the linear movement excursions of the said membrane are interpreted as pressure of the fluid inside the inflow tube 11 by a suitable pressure transducer. Such type of pressure sensor being directly incorporated in the wall of the inflow tube 10 senses the fluid pressure without the intervention of tube 24. The basic purpose of the transducer 14 is to measure the fluid pressure inside the inflow tube 11, such as at point 26, thus the mechanical construction of the transducer is not important as long as it measures the fluid pressure. For the sake of simplicity the existence of tube 24 shall be continued to be considered in the rest of the manuscript. The peristaltic pump 20 attached to the outflow side actively extracts fluid out of the tissue cavity 15 via the out flow tube 18. The outlet end of the pump 20 is connected to a waste fluid carrying tube 21 which opens into a waste fluid collecting reservoir 22 at atmospheric pressure. The rollers of the pump 20 constantly compress and roll over the entire length of the peristaltic pump tubing 19 thus displacing fluid in the direction of the curved arrow which also corresponds with the direction of pump rotation.

In order to understand the invention in a simpler manner all the tubes shown in FIG. 3 and the inflow and out flow port are considered to be having the same uniform inner diameter. However the inner diameter of the tubes and the inflow and outflow ports can also be different. The inflow and outflow ports are metallic adaptors located at the proximal end of the endoscope and are meant to connect with the inflow and outflow tubes respectively, however the said inflow and outflow ports have not been separately shown in any of the figures. Tube 19 consists of a soft resilient plastic material which can be efficiently compressed by the rollers of the peristaltic pumps. The other tubes also consist of a suitable resilient plastic material. It is assumed that the bladder 10 along with the fluid container 10, the inflow tube, the cavity, the out flow tube and the out flow peristaltic pump are placed at the same horizontal height with respect to the ground. The bladder cavity enclosing the container 10 can also be hung on a stand at a suitable height above the patient but in this case the additional pressure as a result of the fluid column in the inflow tube 11 also has to be taken into account. Thus for an easier understanding bladder cavity 10, the inflow tube 11, the cavity 15, the out flow tube 18 and pump 20 shall be assumed to be at the same horizontal height with respect to the floor. Also the rollers of pump 20 should press adequately over tube 19 in such a manner that there is no leak through this tube when the pump 20 is stationary. It is also assumed that there is no abnormal leak of fluid in the irrigation system, for example leak via a accidental hole made in any irrigation tube or a fluid leak which might occur if the endoscope loosely enters into the tissue cavity, for example in hysteroscopic surgery fluid leaks by the sides of the endoscope if the cervix is over dilated.

Figure 4:
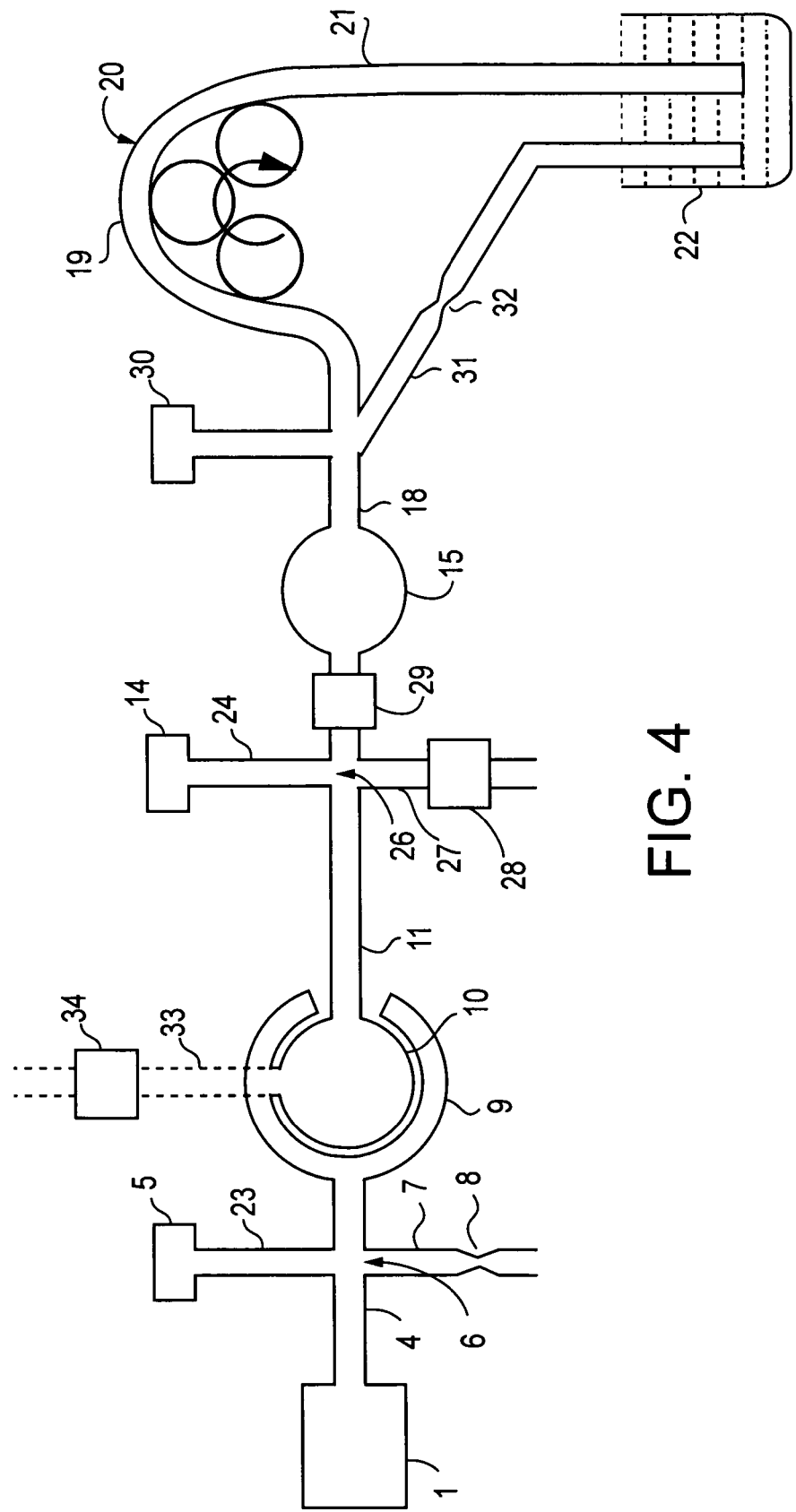
FIG. 4 is the same as FIG. 3 except that a fluid replenishing tube, an optional transducer on the outflow side and an optional constriction site housing tube have been included.

Also a constriction site housing tube similar to tube 7 labeled as 31 can be attached to the outflow tube 18 as shown in FIG. 4. In the said tube 31 the said constriction site is labeled as 32. Such tube can serve a number of purposes. Tube 31 can be utilized for relatively faster evacuation of air bubbles from the cavity. The said bubbles are invariably created inside the cavity as a result of electrosurgical cutting and coagulation or they may enter the cavity while the endoscope is being introduced into the cavity. Such bubbles cause extreme nuisance for the surgeon because they obscure vision and thus the surgical time may be greatly increased. In routine surgery the surgeon moves the tip of the resectoscope near the bubble and the bubble is sucked out of the cavity by the process of continuous flow irrigation. However in certain situations it may not be possible to bring the tip of the resectoscope near the bubble, one such situation is when bubbles accumulate inside a very deep cornuae associated with a long septum, the diameter of the cornuae being less than the outer diameter of the resectoscope. In such a situation the tubal opening situated at the center of the cornuae can only be visualized after evacuating such bubbles from the cavity. In such situation the bubbles can be quickly evacuated without moving the tip of the resectoscope near the bubbles by simply opening the constriction 32 in the tube 31. However such maneuver tends to completely collapse the cavity. Thus if the resctoscope tip is only moderately away from the bubbles the constriction site 32 is opened only partially so that the bubbles are sucked out and the cavity collapses by a relatively smaller magnitude. In place of the adjustable constriction site 32 a pressure release safety valve may be incorporated as a safety feature, however it is more beneficial to install such pressure safety valve in the inflow circuit. The tube 31 may also be used for quickly flushing air bubbles from the irrigation tubes by fully opening the constriction site 32 for a few seconds. The tube 31 may also be used for any other purpose as deemed fit by the surgeon. However the said tube 32 has intentionally not been included in FIGS. 1 to 3 only to keep the drawings simple. However tube 31 is a very beneficial component and is thus recommended to be incorporated in the system of the proposed invention. The opening and closing of the constriction site 32 can also be regulated manually to help in various special advanced endoscopic applications. Incorporation of tube 31 with the variable constriction site 32 can help in reducing the substantially high amplitude pressure variations inside the cavity caused by abnormally large cavity wall contractions, but such phenomenon is only rarely encountered. Also an additional pressure transducer 30, as shown in FIG. 4, may also be attached on the out flow tube 18, if desired, as shown in FIG. 4. However the said pressure transducer 30 has intentionally not been included in the main block diagrams of the invention because by doing so it would have become very difficult to explain the basic physical principals of the invention. Also a fluid replenishing tube 27 with a flow controlling valve or clamp 28, as shown in FIG. 4 can also be incorporated. A flow controlling valve or clamp 29, as shown in FIG. 4, can also be incorporated in the inflow tube 11. The function of the said 27, valves 28 and 29 shall be described in the subsequent paragraphs. The said fluid replenishing tube can also be connected directly to the fluid source reservoir 10 and such tube has been labeled as 33 and the related flow controlling valve has been labeled as 34.

In order to clearly understand the system shown in FIG. 3 it would be helpful to first discuss the functioning of the inflow pneumatic pump 1. As already mentioned the pneumatic pump 1 is a piston pump. Initially when the pump 1 is not operating the tubes 4, 23, 7 and the bladder cavity 9 contain air at atmospheric pressure. When the pump 1 is operated air starts entering into tubes 4, 23, 7 and the bladder cavity 9. The moment the constriction site 8 is fully occluded air starts accumulating inside tubes 4, 23, the bladder cavity 9 and a part of tube 7 between point 6 and the constriction site 8. If tube 7 continues to remain fully occluded at the constriction site 8, the air continues to accumulate inside tubes 4, 23, the bladder cavity 9 and a part of tube 7 between point 6 and the constriction site 8 and the pressure transducer 5 reads a steeply increasing air pressure. The moment the block at the constriction site 8 is partially released air escapes in the form of a jet through the partially open constriction opening 8 into the atmosphere. With the constriction opening 8 being only partially blocked, if the pump 1 continues to work at constant RPM the air pressure ultimately gets stabilized at a fixed value provided the internal diameter of the constriction site 8 is not further varied. The diameter D of the constriction site 8 ranges from a minimum non-zero value to a maximum value which is less than the overall diameter of the rest of the housing tube 7. Henceforth in this manuscript the inner diameter of the constriction site 8 shall be deemed to be fixed at some predetermined value D, unless otherwise stated. The fluid which is being expelled out of the fluid source container 10 is actually pulsatile in nature due to the pulsatile nature of the air pressure inside the bladder cavity 9. A system to dampen the pulsatile nature of the air pressure shall be described in the later sections of this manuscript. The pressure sensed by the pressure transducer 5 is equal to the pressure inside the bladder cavity 9, as it simulates a static system. Further the pressure inside the bladder cavity 9 can be considered almost equal or slightly higher than the pressure inside the fluid source container 10. Due to frictional resistance experienced by the moving fluid the pressure at point 26, as sensed by the transducer 14, is always found to be higher than the actual pressure inside the tissue cavity 15 but the said pressure difference is so small that it may be neglected from the practical surgical point of view. Also such pressure difference increases as the fluid flow rate increases. In the out flow rate ranging between 0 to 500 ml/min such pressure difference is in the range between 0 to 2 mm Hg approximately. The term 'out flow rate' is being referred to the flow rate of pump 20. Also, the said pressure difference remains constant all through surgery at any fixed outflow rate. Though the said pressure difference is negligible but if desired its effect can also be totally negated by subtracting its value from the pressure reading of the transducer. In this manner, in endoscopic surgeries, it is possible to determine the actual cavity pressure by using the pressure transducer 14 located far away from the cavity. This feature is of special relevance because in endoscopic procedures like hysteroscopy, arthroscopy and brain endoscopic surgery while it is important to know the actual cavity pressure but at the same time it is practically difficult to take a pressure measurement directly from the cavity.

Referring to FIG. 3 it shall be first described as to how the system of the proposed invention can be used mechanically, that is without a controller. The peristaltic pump 1 and the peristaltic pump 20 can be made to work at any fixed rotational speed. The air flow rate of pump 1 and the fluid flow rate of pump 20 is directly proportional to the pump RPM or the pump rotational speed. Thus any precise pump flow rate can be generated by selecting a suitable pump rotational speed. The fluid flow rate of pump 20 shall henceforth be denoted by R2 and shall be termed as the 'outflow rate'. The air flow rate of pump 1 shall be denoted by R1 and shall be termed as the 'inflow rate' Here it is to be noted that the term 'inflow rate' R1 is not the inflow rate for the cavity 15, as might be suggested by the literary meaning of the term 'inflow'. Henceforth in the entire manuscript the term 'inflow rate' shall only be referred to the flow rate of the inflow pump 1 unless specifically mentioned. However the term 'outflow rate' R2 does correspond to the literary meaning of the term 'outflow' because R2 is equal to the rate at which fluid flows out of the cavity 15. The surgeon initially decides an out flow rate R2 by selecting a suitable rotational speed for pump 20. Next the surgeon decides the maximum flow rate at which fluid could be allowed to enter into the tissue cavity via the inflow tube 11 and the inflow pump 1 is set to work at such flow rate or at a flow rate slightly lesser than this. Intravasation is process by which fluid enters into the patient's blood circulation through the cut ends of blood vessels located in the cavity wall or enters into the patient's body, for example into the peritoneal cavity, as a result of an accidental perforation or escapes via patent fallopian tubes into the peritoneal cavity. Thus 'intravasation' is a process by which the pressurized irrigation fluid enters into the patient's body system through the walls of the tissue cavity. In case of a surgical accident like cavity wall perforation the fluid being squeezed out of the container 10 can enter into the patient's body at a rate slightly less than the value R1. It is obvious that the maximum rate of fluid intravasation cannot exceed the value R1. In case of an accident like cavity wall perforation it may take some time before an abnormally high intravasation rate is discovered and in such time a dangerous quantity of fluid might enter into the patient's body. If the inflow rate R1 is kept at a relatively lower value then the volume of intravasated fluid in case of such an accident would be low. After fixing the values for R2 and R1 the system is started and the diameter of the constriction site 8 is gradually reduced. As the diameter of the constriction site 8 is reduced air pressure starts building up inside the bladder cavity 10 as a result of which fluid starts flowing into the tissue cavity and the pressure inside the tissue cavity starts rising. When the desired pressure is achieved inside the tissue cavity the diameter of the constriction site 8 is not reduced any further and is fixed. The diameter at the constriction site is termed as "D". The constriction site may also be a plastic or metal piece which has a hole in the centre such that the diameter of the hole is permanently fixed at some value D. If a constriction 8 has a permanently fixed diameter then only the flow rates, that is the RPM's, of pumps 1 and 20 have to be set before the system becomes operational.

The Inventors here would like to discuss about the importance of incorporating the housing tube 7 with the constriction site and the non-obvious advantages provided by the housing tube 7 with the constriction site.

As mentioned earlier, till date the surgeons were left with only two options, either to ignore the cavity pressure variations by not correcting them, or to externally and actively correct such pressure variations. To externally and actively correct the variations in the cavity pressure, controller was incorporated and the working of the pumps were essentially controlled by the controller. Incorporation of the controller controlling the operation of the pumps did not provide any benefit The controllers used to activate the controlling action after the variations in the cavity pressure had subdued. Thus, the controlling action initiated by the controller instead of benefiting the surgeon leads to an undesirable turbulence inside the cavity and also tends to amplify the resultant movement excursions of the cavity walls. The Inventors have noticed that if the controller continuously controls the operations of the pumps (either on the inflow side or on the outflow side), the cavity pressure continuously fluctuates around a preset value and it not at all possible to attain a constant value. The Inventors believe that the controller provides proper corrective action (by continuously controlling the operations of the pumps) only if the fluctuations in the cavity pressure are gradual and not highly instantaneous. That is, if the quantitative rise/fall in the cavity pressure is over long time period, the controller would be able to provide proper corrective action. As the time period to detect variation in the cavity pressure and commence corrective action is ideally in the range of 2 to 4 seconds, if the quantitative rise/fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus it takes very long time period for the system to once again get stabilized.

The Inventors have surprisingly found that by incorporating a housing tube 7 provided with a constriction site in the air carrying tube 4 as described above, inherently and passively corrects the pressure variations due to physiological cavity wall contractions and the mechanical movement of the tubes and the endoscope and also limits the variation in the size of the cavity. The Applicants would like to highlight that it is important to control both the variations in the pressure inside the cavity and the changes in the size of the distended cavity. Large variations in the pressure inside the cavity or the size of the cavity are detrimental to the surgical procedure. In all the prior art systems attempts were made to either control the variations in the pressure or the variations in the cavity size. But none of the prior art document the need to control both the cavity pressure variations and the cavity size variations and hence failed to provide a safe and ideal system. During the contraction of the cavity, a minute quantity of the fluid is pushed out of the cavity. If during this stage the system does not provide a way for releasing the fluid being pushed out, the instantaneous pressure inside the cavity increases tremendously which is harmful to the patient. On the other hand, if the amount of fluid being pushed out of the cavity is not checked/controlled, the changes in the size of the distended cavity are very high. The incorporation of the housing tube having the constriction site for the first time in the present system controls both the variations in the pressure inside the cavity and the changes in the size of the distended cavity. If the cavity contracts some fluid enters the fluid source container 10 in a retrograde manner which causes a minute increase in the volume of the container 10 which in turn reduces the volume of the bladder cavity 10 by a corresponding magnitude and the same is facilitated by the escape of an additional equivalent volume of air via the constriction site 8. Thus the housing tube having the constriction site indirectly provides a by-pass route for the fluid being pushed out of the cavity to go back to the fluid source reservoir 10. This avoids the instantaneous pressure surge inside the cavity which is harmful to the patient The size of the diameter at the constriction automatically controls the amount of fluid passing through the housing tube, thereby controlling the amount of fluid being pushed out of the cavity. Inclusion of the housing tube with the constriction site therefore minimizes the instantaneous variations in the size of the distended cavity.

Alternatively if the cavity expands a suitable volume of fluid is sucked into the cavity from the fluid source container 10, and this is accompanied by a corresponding transient decrease in the flow rate at which air escapes via the constriction site 8 but if the magnitude of the said physiological expansion is more air may even be sucked into the cavity via the constriction site 8. This implies that the constriction site 8 is helping in maintaining a stable cavity pressure despite physiological cavity wall contractions by suitably varying the magnitude as well as the direction of an imaginary air flow vector passing through the constriction site 8.

Cavity Pressure or the Outflow Rate, Both can be Altered Independently without Varying the Value of the Other Parameter:

Referring again to FIG. 3 an hypothetical endoscopic procedure is being considered where surgery is being performed at an outflow rate R2 and inflow rate R1 with the constriction 8 diameter being been fixed at some value D and a resultant cavity pressure P being created maintained. In such hypothetical situation as long as R2 and R1 are not altered the cavity pressure P remains predictably constant throughout surgery resulting in a predictably stable mechanical distension of the tissue cavity walls which culminates in constant clear visualization throughout the endoscopic procedure. If in the said hypothetical procedure the cavity pressure needs to be increased without altering the out flow rate R2 then all that is needed is to start increasing the value of R1 and stop doing so when the desired higher cavity pressure is achieved. Similarly if the cavity pressure needs to be decreased without altering the out flow rate R2 then R1 is decreased till the desired lower cavity pressure is attained. In the said hypothetical endoscopic procedure if the outflow rate R2 needs to be increased without altering the cavity pressure P then the value of R2 is increased by the desired magnitude but simultaneously the value of R1 is also increased by a similar magnitude. Similarly, if the outflow rate R2 needs to be decreased without altering the cavity pressure P then the value of R2 is decreased by the desired magnitude but simultaneously the value of R1 is also decreased by a similar magnitude. Thus if R1 and R2 are simultaneously increased or decreased by the same magnitude the cavity pressure does not vary, the value D is always fixed as already stated. The preceding statements shall now be explained by the help of a numerical hypothetical example. In reference to FIG. 3 considering a hypothetical situation in which an endoscopic procedure is being done at an outflow rate of 100 ml/minute, an inflow rate R1 and the cavity pressure being 80 mm Hg. If the surgeon wants to increase the outflow rate to 322 ml/minute by maintaining the cavity pressure at the same value of 80 mm Hg outflow rate is increased to 322 ml/minute and the inflow rate is increased by 222 ml/minute, because 322 ml/min−100 ml/min=222 ml/minute. As already mentioned in this paragraph if both inflow and outflow rates are increased or decreased by the same magnitude the cavity pressure does not change. Thus the final inflow rate becomes R1+222 ml/minute, where R1 was the initial inflow rate. Thus in the proposed invention the cavity pressure and the outflow rate both can be altered absolutely independent of each other without affecting the value of the other parameter.

Mechanical Version of the Invention:

The mechanical version of the invention shown in FIG. 3 can be used practically in endoscopic surgeries but it requires a skilled operator having a detailed knowledge of the physical principals involved in cavity distension, which may not be always possible. Also the mechanical version has certain practical limitations which shall be explained in the later sections of the manuscript. This mechanical version of the invention has been discussed only in order to explain more clearly the basic physical principals of the invention.

Controller Based Version of the Invention:

Referring to FIG. 2, this figure shows a schematic diagram of the main invention which is proposed to be used in endoscopic procedures. FIG. 2 and FIG. 3 are similar except that in FIG. 3 the controller system is not included. A tachometer, not shown in the diagrams, is coupled to each pump and sends information regarding the pump RPM's to the controller 25 via wires 3 and 17 respectively. The pump flow rates being proportional to the pump rotation speed the tachometer signals always conveys flow rate related information to the controller. The controller also regulates the rotation speed of the two pumps via electrical signals sent through wires 3 and 17. The pressure transducer 14 conveys the fluid pressure signal to the controller via wires 13. The pressure transducer 5 always sends the bladder cavity pressure related information to the controller via wires 12. The controller can be programmed can be programmed not to allow a build up of air pressure which is more than the maximum allowable cavity pressure. On the basis of a pressure feed back signal received from the pressure transducer 14 the controller regulates the rotational speed of the inflow pump 1. The outflow pump 20 works at fixed outflow rates and the flow rate of this pump is also regulated by the controller via suitable electrical signals sent via wires 16. A provision exists by which desired values for P and R2 can be fed into the controller and the values R1, R2 and P can be continuously displayed via suitable display means incorporated in the controller. The pressure reading of the pressure transducer 5 can also be displayed in the controller. The controller can be programmed to perform many special functions related to endoscopic surgery which shall be discussed in the following paragraphs.

Method of Operating the Controller Based Version of the Invention:

Again referring to FIG. 2, in context with the present invention at the start of surgery the surgeon initially selects suitable values for cavity pressure P and outflow rate R2. The said desired values of P and R2 are fed into the controller via suitable input means incorporated in the controller. The diameter D at the constriction site 8 remains fixed at some pre selected value. The diameter of the constriction site 8 is so chosen that it suits the operational needs of the endoscopic procedure. When the system shown in FIG. 2 is operated the controller 25 instructs the outflow pump 20 via wires 16 to continuously extract fluid out of the body cavity 15 at a desired fixed outflow rate R2. Thus all through the surgery the outflow rate remains fixed at R2 irrespective of any internal or external factors unless intentionally changed by the surgeon. The cavity pressure is sensed by the pressure transducer 14 and a corresponding pressure feedback signal is sent to the controller via wires 13 on the basis of which the controller regulates the inflow rate R1, via wires 2. After the system is made operational the controller 25 gradually increases the inflow rate up to the point where the desired preset cavity pressure P is achieved. Let the value of the inflow rate at which the desired cavity pressure is achieved be termed as 'R1.Final'. It is obvious that the value 'R1.final' is actually determined by the controller by a pressure feed back mechanism and such determination of the value 'R1.Final' is based on the preset values of R2 and P. The controller is so programmed that once the value 'R1.Final' is achieved and is maintained for a desired minimum time interval, for example 10 seconds, after which the controller releases the inflow pump 1 from its pressure feedback control mechanism and allow the inflow pump 1 to operate on its own at an inflow rate 'R1.Final' which was determined by the controller. In this manner the two positive displacement pumps continue to work at fixed flow rates to maintain a desired stable cavity pressure. The controller is also programmed that in case the cavity pressure subsequently alters, for example due to intravasation, by a desired minimum preset magnitude and for a desired minimum time, which may hypothetically be 10 seconds, the inflow pump 1 again comes under the pressure feedback control of the controller and a new value of 'R1.Final' is determined by the controller after which the inflow pump 1 is again allowed to be operated without the pressure feedback mechanism at the newly determined 'R1.Final' inflow rate. Such sequence of events continue to occur throughout the endoscopic procedure. Taking an imaginary example if the total surgical time is 60 minutes then it may be hypothetically possible to operate the inflow pump independent of the pressure feedback mechanism for 55 minutes and under the control of the pressure feedback mechanism for 5 minutes. However, provision of operating the inflow pump 1 under a pressure feedback mechanism all through the endoscopic procedure can also be incorporated.

The Advantage of Operating the Inflow Pump Independent of the Pressure Feedback Mechanism:

The only reason for operating the inflow pump 1 independent of the pressure feedback mechanism is to avoid unnecessary corrections of minor pressure variations caused by physiological cavity wall contractions and the mechanical movements of the irrigation tubes. The concept of physiological cavity wall contractions has been explained-in detail under the heading 'basic physics of cavity distension'. In the present invention the physiological variations in cavity pressure are automatically corrected by the constriction site 8 without the need of a controller. If the cavity contracts a minute quantity of fluid which is pushed out of the cavity and this causes a corresponding volume of air to escape vie the constriction site 8. It is to be noted that the distal end of tube 7 is open at atmospheric pressure thus air escapes via the constriction site 8 against a zero pressure head, which is atmospheric pressure. Thus, the transient, insignificant and instantaneous rise/fall in cavity pressure variations get stabilized at the desired preset value within a fraction of seconds. Alternatively if the cavity expands a suitable volume of fluid is sucked into the cavity from the fluid source container 10 and this is accompanied by a corresponding transient decrease in the flow rate at which air is escaping via the constriction site 8 but if the magnitude of the said physiological expansion is more air may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8. Normally the direction of such imaginary vector is always towards the open distal end of tube 7 while its magnitude constantly varies to take care of the pressure changes resulting due to physiological cavity contractions. Normally a cavity continuously contracts and dilates by approximately the same magnitudes thus there is little logic to check the minor pressure variations emanating from the said contractions. Also the opening of the constriction site 8 does not allow the said physiological cavity pressure fluctuations to cause any significant cavity wall movement excursions by allowing to and fro movement of air flow through its lumen. However, if the said pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller. As explained in the previous paragraph the controller is so programmed that the inflow pump 1 automatically comes under the pressure feedback control mechanism of the controller in case the cavity pressure alters by a desired minimum preset magnitude and for a desired preset time interval, thus a new 'R1.Final' inflow rate is established at which the inflow pump is again allowed to operate without the feedback control of the controller. As a safety precaution a provision can be made in the controller via suitable input means to fix an upper safe limit for the inflow rate R1, the cavity pressure P and the pressure inside the bladder cavity such that these safe limits are not exceeded accidentally.

Selection of a Suitable Diameter for the Constriction Site:

The most suitable diameter D for the constriction site 8 can be selected for endoscopic procedure or procedures but such an approach must take into consideration the operational efficiency needs in context with the cavity pressure fluctuations which might occur due to the inevitable physiological contraction or expansion of the cavity walls. If the diameter of the constriction site 8 is very small then the said transient pressure fluctuation in the cavity pressure would be of a relatively larger magnitude and would last for a relatively longer time interval but the associated resultant movement excursion of the cavity wall would be of a relatively small amplitude. Similarly if the diameter of the constriction site 8 is very large then the said transient cavity pressure fluctuations would be of a relatively smaller magnitude and would last for a relatively shorter time interval but the associated resultant movement excursion of the cavity walls would be of a much larger amplitude. These statements are explained by the help of three hypothetical numerical assumptions as stated in table 2 which is as follows:

TABLE 2

| Serial number of the assumption | A hypothetically assumed numerical value of the construction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.05 mm | 20 mm Hg | 3 seconds | 0.5 mm |
| 2 | 0.1 mm | 5 mm Hg | 1 second | 1 mm |
| 3 | 0.9 mm | 1 mm Hg | 0.5 seconds | 5 mm Hg |

(Note: A similar table can be hypothetically constructed taking into consideration cavity wall expansion, instead of contraction.)

In context with routine endoscopic procedures the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus the nuisance value of a cavity wall movement excursion is relatively more than the nuisance value of the said transient pressure surge. However the amplitude of the pressure surge should also be not very high because it may promote intravasation and other problems. Thus while selecting the diameter of the constriction site two things are kept in mind, the operational needs of the endoscopic procedure and the anticipated cavity wall contraction and expansion movements. Thus in those endoscopic procedures where mechanical stability of the cavity walls is important the numerical value of the constriction site diameter D should be relatively smaller. There may be endoscopic precedures where mechanical stability of the cavity walls is not the major concern and in such case a relatively higher value of D may be chosen.

Limiting and Predicting Cavity Pressure Surge in Case of Accidental Outflow Obstruction:

If an abnormally high pressure develops inside a tissue cavity during endoscopic surgery it may cause mechanical rupture of the cavity and may also lead to dangerous intravasation. Referring to FIG. 2 if during endoscopic surgery the outflow tube is accidentally blocked the cavity pressure does not increase to dangerous levels because the controller automatically instructs the pump 1 to work at a reduced RPM, thus a surgical complication is avoided. Referring to the system shown in FIG. 3 if the outflow tube 18 is accidentally blocked the cavity pressure rises to a dangerously high value in the absence of a controller. In context with FIG. 3 an accidental obstruction of the outflow tube or a deliberate obstruction of the inflow tube as achieved by willfully closing the inflow port, both the situations result in a steeply rising pressure as measured by the transducer 14. Thus, while using the mechanical version of the invention as shown in FIG. 3, it is suggested that before starting the endoscopic surgery the surgeon should deliberately block the distal end of the inflow tube 11 by closing the inflow port of the endoscope and note the resultant maximum pressure rise. If the resultant pressure is higher than the maximum prescribed safe cavity pressure, then the diameter of the constriction site can be increased by some magnitude such that the resultant pressure created by blocking the inflow tube is well below the maximum safe pressure prescribed for the tissue cavity. In this manner, for a mechanical system as shown in FIG. 3, for a specific inflow rate R1, the maximum resultant pressure that would develop inside the cavity in the case of a block in the outflow tube can be predictably known and limited. Such method of knowing and limiting the rise in cavity pressure as a result of outflow tube obstruction does not have much role in the controller based version of the invention as shown in FIG. 2. However, even if the controller based version of the invention as shown in FIG. 2 is being used and a high out flow rate is being used then if the outflow tube is suddenly obstructed a transient pressure surge of a relatively small or large amplitude may be experienced before the controller finally stabilizes the inflow pump rotation speed at a significantly reduced value to maintain the initially desired preset cavity pressure. Such pressure surge occurs because initially the pressure transducer senses an exponentially increasing cavity pressure, next a corresponding feedback signal is sent to the controller and the controller finally acts by reducing the rotational speed of the inflow pump and all these actions may take a few seconds to be implemented, especially if the inflow pump was operating at a very high speed of rotation, and in this short time interval a transient surge in the cavity pressure may be experienced. The amplitude of such pressure surge would be small due to the controller feedback mechanism but even a small magnitude surge may damage fragile tissues, for example tissue inside a brain tissue cavity. The amplitude of the said surge can be predictably reduced by suitably increasing the value D. Thus a relatively higher value of D enhances patient safety by predictably limiting the maximum pressure which can develop inside the cavity in case of an accidental obstruction of the outflow tube 18 if the mechanical version of the invention is being used and it also predictably limits the amplitude of any small amplitude pressure surge which might occur when the inflow tube is accidentally blocked while the controller based version of the invention is being used. It has been described in the previous paragraph that the operational efficiency of the system also improves if the value of D is increased. Thus a suitable value of D can be selected by keeping into consideration patient safety and system efficiency. Once a suitable value for D is selected it never altered thereafter as has already been discussed previously. The systems shown in FIGS. 2 and 3 can also have the provision of incorporating constriction sites having different diameters D to suit and accommodate the operational needs of multiple type of endoscopic procedures.

Methods of Shortening the Cavity Refilling Time:

The advantage of shortening the cavity refilling time has already been discussed in a preceding paragraph and in the present invention this beneficial maneuver can be carried out by the help of the controller. Referring to FIG. 2, one simple way of reducing the cavity refilling time is by temporarily increasing the fluid flow rate into the cavity while the cavity is being filled. The physical principals related to the said maneuver shall now be described. Referring to FIG. 2 let the difference in the values of R1 and R2 be denoted by a value R which can be stated in equation form as R=R1−R2. Also R1 has to be always more than R2 if any positive cavity pressure is to be maintained. In the system shown in FIG. 2 it is seen that if the cavity pressure is fixed at a preset value P then the value R=R1−R2 also never changes irrespective of the desired outflow rate. The value D is always fixed as already discussed. This implies that in the normal operational mode, for any fixed value of P, the value R=R1−R2 always remains the same. However, when the inflow port is deliberately closed the pressure transducer 14 senses an increased pressure due to which the inflow rate is significantly reduced by the pressure feedback circuit, the outflow rate being always fixed at a value R2. In a mathematical manner it can be stated that if the inflow port is deliberately closed the value R reduces while the pressure value P remains unchanged. A reduction in the value R of a certain minimum magnitude associated with an unchanged P can serve as a trigger which prompts the controller to carry out a specified sequence of events. Let such trigger be termed as 'refilling initiation trigger'. The controller can be so programmed such that upon being prompted by the 'refilling initiation trigger' the controller can carry out any one of the below mentioned three maneuvers A, B or C:

1. Maneuver A: The moment the controller is prompted by a 'refilling initiation trigger' the controller makes the pump 5 to work at some increased flow rate such that a pressure P1, which usually would be higher than the desired cavity pressure, is created and maintained in the fluid source container 10. The value of P1 is so selected that when the inflow port is opened after reintroducing the endoscope the cavity gets completely filled up in a desired shorter time interval and at the end of such a maneuver the cavity pressure also should not exceed a prescribed maximum safe cavity pressure or a lower value as desired by the surgeon. Subsequent to opening the inflow port the pressurized fluid accumulated in the inflow circuit enters the cavity in the form of a transient high velocity jet lasting for a few seconds, due to which the cavity gets filled at an accelerated pace thus reducing the total refilling time. The cavity refilling time can thus be reduced by programming the controller to create and maintain a suitable higher value of P1 but it is also important that the value P1 should be low enough such that at the end of the refilling phase, that is when the cavity is completely filled, the pressure inside the cavity does not exceed the maximum prescribed safe cavity pressure. The moment the inflow port is opened the pressurized fluid enters into the cavity and pressure transducer 14 immediately senses a fall in pressure below P1. The controller has to be further programmed that such that any further fall in pressure below P1 should serve as a second trigger which prompts the controller to start working in the normal mode. By normal mode it is meant that the controller functions in order to maintain a desired cavity pressure at a desired outflow rate as was initially decided at the beginning of the surgery. The only draw back in this proposed method of reducing the cavity refilling time is that an accidental kinking of the outflow tube 18 may be wrongly sensed by the controller as deliberately blocking the inflow port. But such accident can be avoided by fixing a suitable upper limit for the cavity pressure or to just accept the remote possibility of such a remote accident but the maximum cavity pressure created in such an eventuality is known and can also be limited. Some hypothetical numerical examples shall be taken in order to further clarify the steps proposed in this paragraph. It is practically seen in hysteroscopy that if the value P1 is taken as 160 mm Hg a uterine cavity having a volume capacity about 20 ml gets filled in approximately 2 seconds and at the end of which a uterine cavity pressure of 60 mm Hg is created. If the cavity had been allowed to fill at a normal flow rate used in actual surgery, for example 50 ml/minute, it would have taken 24 seconds to completely fill a cavity having the same volume capacity. However if a bladder cavity having a large volume capacity of up to 300 ml is substituted in place of the uterine cavity the proposed 'method A' cannot be used for reducing the cavity refilling time. Methods B and C are being proposed to reduce the cavity refilling in the case of large cavities like bladder cavity.

2. Method B: Let us take a hypothetical example of a bladder cavity having volume capacity of 300 ml and the desired cavity pressure while doing the endoscopic surgery being 30 mm Hg. As explained in method A the controller is programmed to create a pressure P1 when the inflow tube is deliberately blocked after withdrawing the endoscope. In method A the opening of the inflow port after again introducing the endoscope into the cavity, serves as the second trigger for the controller to start working in the normal operational mode to maintain a desired cavity pressure and at a specified outflow rate but in method B the controller is programmed differently such that opening the of inflow port after again introducing the endoscope into the cavity should serve as the second trigger which prompts the controller to work at an increased flow rate for a specified time, such time being the calculated time interval in which the cavity would get completely filled, and after the expiry of such specified time the controller being further programmed to start working the system in the normal operational mode. Taking an hypothetical example with numerical values, if the value P1 was taken as 160 mm Hg, as was assumed in method A, then 20 ml fluid shall accumulate inside the bladder cavity in 2 seconds but still 280 ml=300 ml−20 ml more fluid needs to be introduced inside the bladder cavity in order to fill it completely. Hypothetically, the controller may be so programmed that opening of the inflow port should serve as a second trigger to the controller to make the inflow pump 5 work at an inflow rate of 1000 ml/minute for 16.8 seconds. At such flow rate 280 ml fluid can be pushed into the bladder cavity within 16.8 seconds. Had the bladder cavity been filled at an inflow rate of 50 ml/min it would have taken 6 minutes for the cavity to get completely filled where as by resorting to method B the cavity filling time is reduced to 18.8=2+16.8 seconds.

3. Method C: Let the 'refilling initiation trigger' serve only as a trigger which informs the controller that the inflow port has been deliberately blocked and the controller should be so programmed that it allows the inflow pump to continue working in the normal operational mode, that is to maintain the desired cavity pressure. The opening of the inflow port can serve as the second trigger which prompts the controller to make the inflow pump work at an increased flow rate for a specified time and then to again start working in the normal operational mode. This would reduce the cavity refilling time significantly. Taking a hypothetical example similar to the example taken in method B, if opening the inflow port serves as a trigger to make the inflow pump work at a flow rate of 1000 ml/min for 18 seconds then the bladder cavity would get completely filled in 18 seconds.

It is to be noted that in this paragraph the term 'inflow rate' is not the rate which fluid enters into the cavity via the inflow tube 11 but it is the flow rate of pump 1.

Measurement of the Actual Cavity Pressure:

In the system shown in FIGS. 1, 2, 3 and 4 the value P refers to the actual fluid pressure inside the cavity 15, but in reality P is a pressure value which is sensed by the transducer 14 in the inflow tube, such as at a point 26 which is situated in the upstream part of the inflow tube 11, far away from the cavity. In any system the most convenient place for installing the pressure transducer is inside the main pump housing. As already discussed a transducer located in such position may not measure the actual pressure inside the cavity. In the out flow rate ranging between 0 to 500 ml/min such pressure difference is in the range between 0 to 2 mm Hg approximately and the said pressure difference remains constant all through surgery at any fixed outflow rate. Thus in the proposed invention the pressure P measured by the transducer 14, being only negligibly higher than the actual cavity pressure, may be considered to represent the actual cavity pressure.

Avoid Changing the Fluid Source Reservoir Container:

The collapsible fluid source reservoir 10 can contain only a limited quantity of irrigating fluid usually ranging between 500 ml to 2.5 liters. During an endoscopic procedure when the irrigation fluid contained inside the reservoir 10 is consumed then the same is replenished by removing the empty container 10 and replacing it with a fresh container 10 which is full of the irrigation fluid. Such maneuver wastes valuable surgical time. In FIG. 4 a fluid supply tube 27 containing a fluid flow control valve 28 has been proposed. In case the fluid source container 10 empties during an endoscopic procedure the irrigation fluid can be instilled at a suitably fast rate via the said tube 27 by fully opening the valve 28 and simultaneously fully closing the valve 29, shown in FIG. 4, and also simultaneously making the value of the inflow rate R1 equal to zero or a negative value. The said fluid control valves 28 and 29 may also be clamps which are applied externally over tubes 27 and 11 to completely block or open the lumen of the said tubes. In order to aid the said irrigation fluid replenishing maneuver the diameter D of the constriction site 8 can be temporarily increased to the maximum possible value or a suitable controlled air releasing vent may be incorporated in the air supply tube 4 or in the pump itself. Further the controlled may be programmed to control the valves 28 and 29, the said air release vent and pump 1. For example the controller may be so programmed that when the irrigation fluid is being replenished via tube 27, then by a single command the valve 28 is fully opened, valve 29 is fully closed, an air release vent attached to tube 4 is fully opens and the pump 1 temporarily stops. Alternatively a fluid supply tube such as tube 33 having a fluid flow control valve 33 may be directly connected to the fluid source reservoir 10 as shown in FIG. 4. The fluid supply tube 33 has been depicted by depicted by two dashed parallel lines. The advantage of incorporating tube 33 is that this tube can have a have a relatively large inner diameter which would promote a more rapid filling of the fluid source container 10. While in context with tube 27 even if the inner diameter of this tube is increased the rapidity at which the fluid source reservoir 10 could be filled would be limited my the smaller diameter of the inflow tube 11. Also irrigation fluid could continuously be instilled into the fluid source reservoir 10 via tube 33 or 27 at a flow rate 'R.Replinish' by utilizing a positive displacement pump such as a peristaltic pump. The value 'R.Replinish' obviously has to be lower than the value R2. However in order to incorporate such concept suitable modifications have to be made, both structural and controller based. After suitable structural modifications such as installation of the second peristaltic pump the controller has to be so programmed that if fluid is instilled into the fluid source reservoir at a rate 'R.Replinish' then the inflow rate should automatically reduce to a suitable value, such as (R1−R.Replinish). It is obvious that the controlled can be programmed in multiple ways in context with the instilling fluid via the tubes 27 and 33. Such provision of instilling fluid via tubes 27 and 33 would avoid interrupting surgery in order to refill the fluid source reservoir 10.

A Variable Constriction Site

In context with the system shown in FIG. 1,2, 3 and 4 it is also possible to have a system in which the cavity pressure is maintained and regulated by continuously varying, by the help of a controller, the diameter D at the constriction site 8. The housing tube having the constriction site is substantially responsible for dampening the pressure pulsation or minimizing the turbulence inside the cavity. It however may not provide any substantial dampening to the pressure pulsation caused by the working of the inflow or outflow pumps. The diameter D at the constriction site 8 could also be intermittently regulated by a controller as and when required for example in the eventuality of fluid intravasation or extravasation thus implying that the diameter D shall be free from the influence of the controller for most of the time and shall be brought under the influence of the controller only when needed and that also for only a small part of the total surgical time. Such a concept has been described in great detail in the previous paragraphs in context with FIG. 2. In the 'variable constriction' system proposed in this paragraph both pumps 1 and 20 would always operate at desired but fixed flow rates and the cavity pressure would be regulated only by varying the diameter D at the constriction site 8. At the start of the surgery the inflow and outflow rates would be set by feeding suitable flow rate values into the controller after which the controller would not influence or regulate the said two pumps and the cavity pressure would be maintained only by varying the diameter D at the constriction site 8. In order to vary the diameter at the constriction site 8 a suitable electromechanical devise such as a solenoid operated devise could be installed over the housing tube 7. Such a devise is not a devise which would either totally close or totally open the lumen of the pipe. By the help of the said devise the lumen diameter would be varied in a controlled manner and not just by totally opening or totally closing the lumen. The said devise could comprise of a long coil containing a movable long cylindrical magnet and this magnet piece by pressing over the tube, would vary the inner diameter of the tube. When current passes through such coil the magnet piece would either be pulled in or pushed out depending upon the direction of the current and the polarity of the magnet and the force which the said long cylindrical magnet piece could apply over the plastic tube would depend upon the current density passing through the coil or in simpler terms the amount of electrical energy supplied to the coil. In context with the present paragraph the controller shall regulated the amount of electrical energy supplied to the coil such that the magnetic rod presses over the tube with an adequate force and the inner diameter of the pipe would depend upon such force. Thus the inner diameter of the tube shall be a function of the current density. The system efficiency of this particular embodiment of the proposed invention could be greatly enhanced by incorporating a system of pump synchronization as described in the next paragraph. However the said solenoid system for the constriction site has not been incorporated in any of the figures only to keep the drawings simple.

A Method to Dampen the Pressure Pulsations Caused by the Outflow Positive Displacement Pump Referring to FIG. 2 the outflow positive displacement pump, that is the outflow peristaltic pump 20 creates pressure pulsations which are invariably transmitted to tissue cavity leading an undesirable turbulence inside the tissue cavity. The fluid pressure is pulsatile in nature because the peristaltic pump 20 constantly extracts fluid from the tissue cavity via the outflow tube 18 in a pulsed manner and not in a continuous manner and this leads to fluid pressure pulsations. The said pulsations are transmitted to the tissue cavity 15 in a retrograde manner via the outflow tube 18. Hypothetically assuming that the pump 20 rotates at fixed RPM then in that case the frequency of such pulsations would remain uniformly the same all through the operation of the pump. If a graph is plotted for the said pulsations, by relating the fluid pressure to the 'Y' axis and the time to the 'X' axis, then such graph-would have a uniform shape having positive and negative pressure swings of a predictably fixed amplitude and fixed frequency. It is to be noted that as the pump RPM is increased the frequency as well as the amplitude of the said pressure swings also increase. The said pulsations are produced because each time any one roller of the peristaltic pump comes in apposition with a fixed point, for example the inlet end of the peristaltic pump 20, some fluid is withdrawn from the outflow tube 18 by the outflow peristaltic pump via its inlet end in the form of a bolus. The wave form of such pulsations need not be sinusoidal, but for the sake of an easier understanding let the said waveform be hypothetically assumed to be sinusoidal in nature. As already stated, if the pump RPM increases then along with the frequency the amplitude of the said waveform also increases. When the pump 20 rotates in the direction of the curved arrow fluid is extracted from the outflow tube 18 the cavity 15 and the inflow tube 11 and let all three of these collectively be termed as 'fluid extraction region'. In physical terms the said pressure pulsations are produced because the fluid tends to be extracted from the 'fluid extraction region' in the form of regular pulses wherein each pulse corresponds to a fixed volume of fluid pulled by a roller from the 'fluid extraction region' in the form of a bolus of fluid. Thus the motion of each roller would correspond to one complete sinusoidal pressure wave. Thus the motion of each roller would correspond to one complete sinusoidal pressure wave, assuming that the said waveform has been assumed to be sinusoidal as previously stated. The movement of a single roller in relation to a fixed point such as the inlet end of the pump can be hypothetically divided into three parts, that is, part one when the roller approaches the said point, part 2 when the roller is in apposition with the said point and part 3 when the roller moves away from the said point. Let the parts 1, 2 and 3 be collectively termed as 'single roller movement' and the time taken to accomplish the said 'single roller movement' be termed as 'single roller time'. Assuming the pressure waveform to be a sinusoidal curve, each 'single roller movement' corresponds to one complete sinusoidal pressure waveform consisting of a positive pressure pulse followed by a negative pressure pulse or vice versa. Also the time period of the assumed sinusoidal wave form would be equal to 'single roller time'. If during a negative pressure pulse an adequate volume of fluid is removed from the 'fluid extraction region' and during a positive pressure pulse the same adequate volume of fluid is again added back into the 'fluid extraction region' the sinusoidal nature of the pressure waveform could get dampened and the resultant waveform would get transformed into an almost straight line curve. The resultant waveform could theoretically be an absolute straight line if the wave form associated with the said process of adding and removing adequate volumes of fluid from the 'fluid extraction region' absolutely resembled with the wave produced as a result of the pulsatile flow of the peristaltic pump and the phase difference between the two waves was exactly 180 degrees however this may not be achieved in practical situations. However a substantial dampening of the resultant waveform could be practically achieved if a syringe system was synchronously coupled with the outflow peristaltic pump 20 and the single outlet end of the said syringe system was connected with the 'fluid extraction region'.

Figure 7:
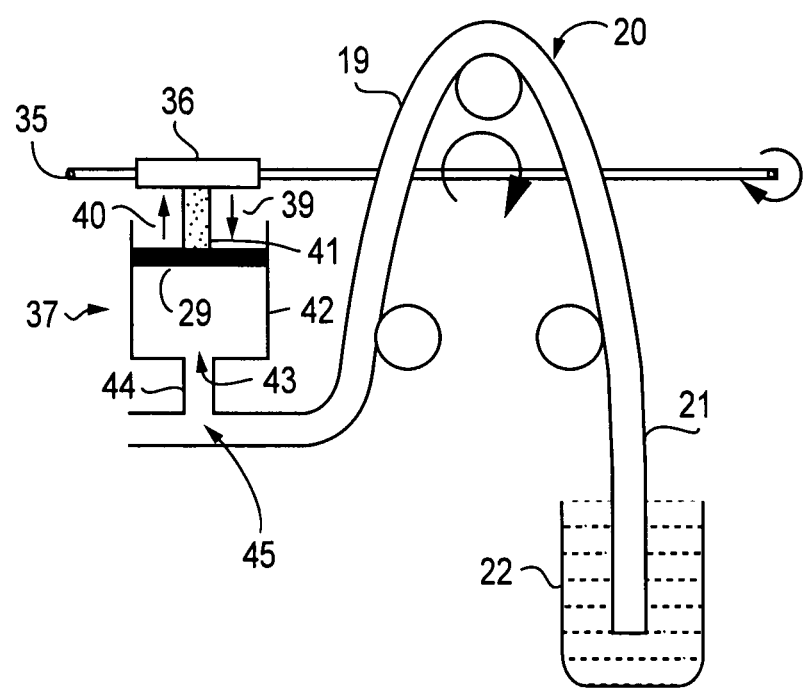
FIG. 7 shows a detailed layout of the outflow pressure pulse dampening system.

The said syringe system is shown in FIG. 7. The syringe system 42 consists of a piston 38 denoted by a shaded area and the piston 38 moves up and down inside a cylinder 42 while making a watertight contact with the inner walls of this cylinder 42. One end of a straight rod 41 is connected to the piston while the other end of this rod 41 is connected to a coupling mechanism 36 housed on a common rotating shaft 35. The coupling mechanism 36 and the peristaltic pump 20, both are attached on this common shaft 35. The coupling mechanism 36 is so designed that it converts the rotary motion of the shaft 35 into a linear up down motion of rod 41 which is ultimately manifested as an up down movement of piston 38 inside the cylinder 42. The up down motion of the rod 41 is denoted by arrows 38 and 40. Thus the shaft 35 is a common shaft which mechanically operates both, pump 20 as well as the syringe system 42. The direction of rotation of the shaft 35 is denoted by a curved arrow located at the right end of the shaft 35. The syringe system 42, as the name suggests, resembles a hypodermic syringe used for giving injections to patients. Obviously, the syringe system 42 has only one single opening 43. A tube 44 extending between the opening 43 and the outflow tube 18 connects the syringe system to the outflow tube 18. Tube 18 is a part of the said 'fluid extraction region' described in the previous paragraph. Thus the syringe system can be considered to be connected with the said 'fluid extraction region'. The opening 43 can be referred to as an 'outlet end' or an 'inlet end' because the syringe system can push as well as pull fluid from the 'fluid extraction region'. However for the sake of convenience henceforth the opening 32 shall be termed as the outlet end of the syringe system 42. The coupling mechanism 36 is so designed that the vertical movements of the syringe system can be accurately synchronized with the rotary motion of the peristaltic pump 20. The piston 38 can move up>down>up or down>up>down, depending upon the initial position of the piston at the start of the motion and let each such movement of the piston be termed as a 'complete piston movement'. The coupling mechanism 36 is so designed that while the peristaltic pump 20 rotates by 360 degrees the syringe system correspondingly exhibits 'complete piston movements' which are equal to the number of the rollers of the peristaltic pump. Thus for a peristaltic pump which has three rollers then for each 360 degrees rotation of the peristaltic pump the syringe system exhibits three 'complete piston movements' while for a peristaltic pump with four rollers four 'complete piston movements' would occur for each 360 degree rotation of the peristaltic pump. The syringe system is synchronized with the peristaltic pump via the coupling mechanism 36 in such manner that while a roller of the peristaltic pump produces a negative pressure pulse the syringe system pushes fluid into the 'fluid accumulation region' and while the same roller produces a positive pressure pulse the syringe system pulls out an equivalent volume of fluid from the 'fluid accumulation region'. In order to dampen the pulsations of the peristaltic pump, besides mechanically synchronizing the syringe system with the peristaltic pump, the volume of fluid pulled in or pushed out of the syringe system corresponding to each upward or downward movement of the piston also has to be accurately adjusted, and the same may be done manually by a 'hit and try method'. The volume of fluid pulled in or pushed out by the syringe system depends upon the linear movement excursion of the piston 38. Also the magnitude of the downward piston excursion is equal to the magnitude of the upward piston excursion, thus the volume of fluid pushed out is always equal to the volume of fluid pulled in during each downward or upward movement. Thus the coupling mechanism 36 has two functions, synchronization of the syringe system with the peristaltic pump and adjusting the volume of fluid pulled in or pushed out by the syringe system for each upward or downward movement of the piston. The synchronization and the determination of the said volume to be pushed out or pulled into the syringe system are done manually such that a substantial dampening of the pressure pulsations is achieved and once this is achieved the synchronization at the level of the coupling 36 is never again disturbed and the volume of fluid pulled in or pushed out of the syringe system for each movement excursion is also not changed thereafter. After the coupling 36 is adjusted with respect to synchronization and the volume of fluid to be pulled in and pushed out, the peristaltic pump pulsations shall continue to remain dampened independent of the peristaltic pump RPM and the nature of rotation, that is fixed or variable RPM. In simpler terms the peristaltic pump pulsations would continue to remain dampened even at a high pump RPM. Also the point at which the syringe system 42 is connected to the said 'fluid extraction region', for example the outflow tube 18, then the position of such a point should also not be changed thereafter because this may bring about a phase difference between the waveform-related to the peristaltic pump pulsations and the waveform related to the syringe system pulsations, thus the resultant dampening could no longer be satisfactory. Also preferably the outlet tube 44 of the syringe system should be connected as close to the outlet end of the inflow peristaltic pump as possible.

Figure 5:
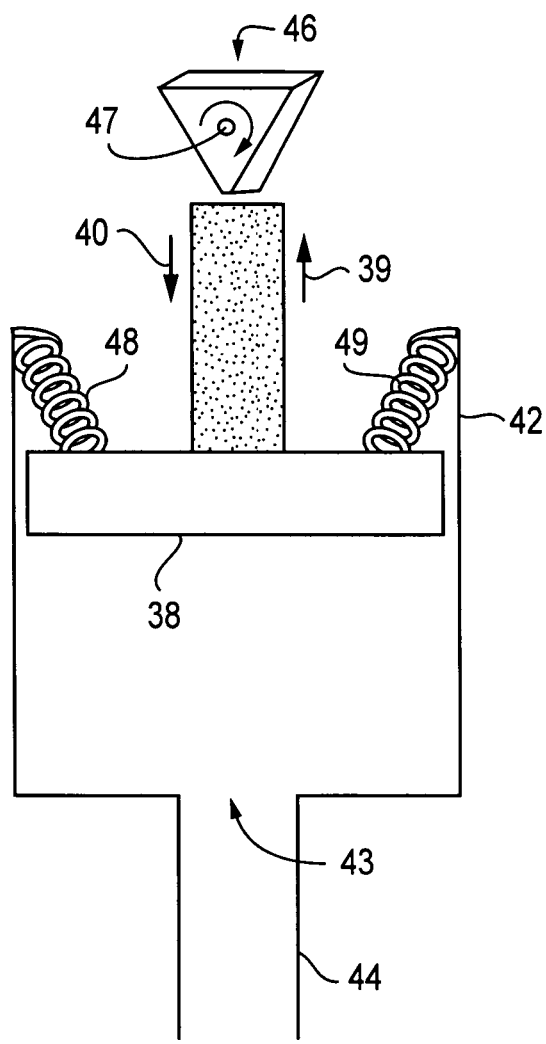
FIG. 5 shown a special type of coupling mechanism to operate the syringe system.

The coupling 36 can be compared to some extent with the conventional CAM system present in automobile engines. Any specific mechanical design for the coupling 36 is not important, it is the resultant function of the coupling 36 with respect to the piston movement, as already described, which is important The coupling 27 can have many mechanical designs. FIG. 5 shows one such possible mechanical design for the coupling 36. In FIG. 5 a small length of the common shaft 35, which is related to the coupling 36, has been made of triangular shape as seen in its cross sectional view and the same is labeled as 46. Let this triangular part 46 be termed as the 'piston coupler'. The edges of the piston coupler are shown sharp however they could preferably be rounded to suit various operational needs. Similarly the size of the 'piston coupler' could also be increased or decreased in order to decrease or increase the volume of fluid displaced by the cylinder during a downward or upward movement of the piston. The central axis point of the 'piston coupler' is denoted by point 47. In case the dimensions of the 'piston coupler' are chosen to be relatively larger than the dimension of the common shaft 35, the point 47 could also represent the point at which the common shaft 35 passes through the 'piston coupler' and in such a situation the 'piston coupler' 46 could be manually rotated on the common shaft 35 in a clockwise or anti clockwise direction and then locked mechanically at a position which provides the most accurate synchronization. The springs 48 and 49 extending between the inner walls of the cylinder and the piston exert a constant and substantially large upward pull on the piston 38 which causes the rod 41 to constantly be in apposition with the 'piston coupler' 46. The springs can be one or more than one in number and the springs can also be substituted by any other mechanical means also which provide an active upward movement of the piston. The 'piston coupler' 46 is assumed to be able to apply a substantially large downward force on the piston 38 via rod 41 such that a corresponding transient negative fluid pressure inside the cylinder can be totally neglected in the face of the said large substantial downward force. Similarly the springs 48 and 49 are capable of pulling up the piston with a substantially large force such that a corresponding transient positive fluid pressure pulse inside the cylinder could be totally neglected. The idea is that the downward movement of the piston should not be aided by the negative pressure pulse inside the cylinder, this downward movement should be an active movement for which energy is to be derived from the springs from the shaft 35. Similarly the upward movement of the piston should not be aided by the positive pressure pulse inside the cylinder, this upward movement should be an active movement for which energy is to be derived from the springs 48 and 49. The energy for the said upward movement of the piston could also be derived from the shaft 35 if suitable mechanical provision facilitating an active upward movement of the piston could be provided at the level of the coupling 46.

It is important to note that it is not mandatory to use the said 'pressure pulse dampening system' with a peristaltic pump only as, with suitable mechanical modifications, the 'pressure pulse dampening system' could be used beneficially with any type of a positive displacement pump.

The 'pressure pulse dampening system' could also be a mechanism like the 'piston coupler' 46 shown in FIG. 5 whose rounded edges could directly impinge on a suitable area situated on the outer surface of the 'fluid extraction region' in a uniform synchronized manner, as described, such that this results in continuous uniform synchronized variations in the total volume capacity of 'fluid extraction region'. The said suitable area on the outer surface of the 'fluid extraction region' could be a membrane made consisting of a strong resilient polymeric material having an adequate elasticity. The said membrane should also be sufficiently thick and should have an adequate elasticity such that an outward movement of such membrane, a movement related to the upward pull by the said springs, applied a substantially larger force in comparison to force related with the transient corresponding pressure pulse.

Figure 6:
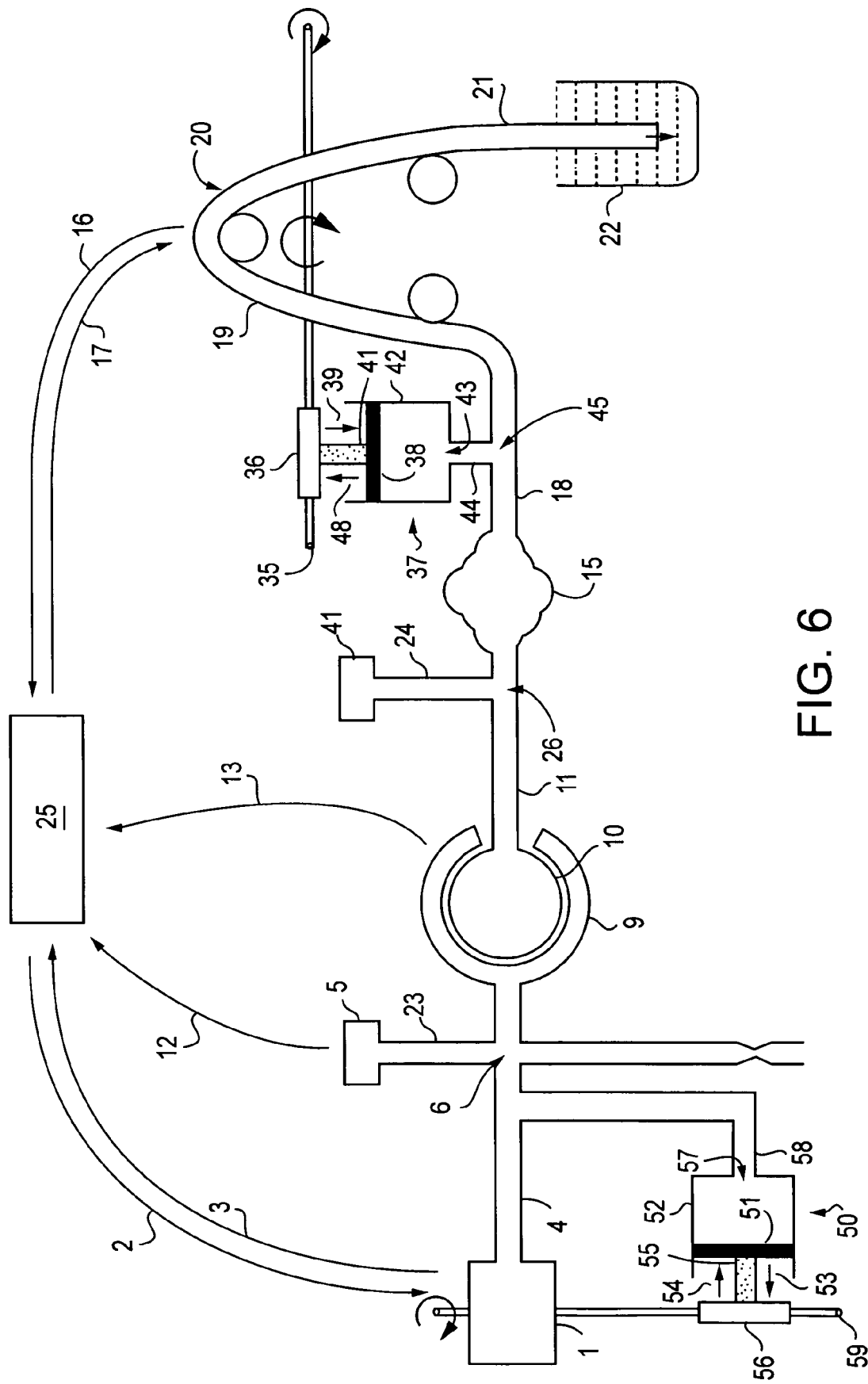
FIG. 6 is similar to the main invention shown in FIG. 1 except that in FIG. 6 a pressure pulse dampening system has been added on the inflow side also.

A Method to Dampen the Pressure Pulsations Caused by the Inflow Positive Displacement Pump A pressure dampening system similar to the one suggested for the outflow side can also be installed on the inflow side as shown in FIG. 6 and the same has been numbered as 50. A common shaft 59 drives both the piston pump 1 and the syringe system via coupling 56 which moves the piston 51 via rod 55 and thus the cylinder moves up and down inside cylinder 52. The outlet end 57 of the syringe system 52 is connected to the air delivery tube 4 via tube 58. The syringe system 52 helps in dampening the air pressure pulsations created by the piston pump 1 in a similar manner as the syringe system 37 helps in dampening the fluid pressure pulse created by the out flow peristaltic pump 20. The air pressure pulsations from the bladder cavity are ultimately transmitted to the tissue cavity via the inflow tube 11 thus leading to undesirable turbulence inside the tissue cavity. Thus it is important to dampen the air pressure pulsations.

The Inventors would like to mention that the pressure dampening mechanism described in the present invention is an active pressure dampening system and not a passive dampening system. The Applicants have realized that only active pressure dampening systems as discussed above provide substantial dampening to the pressure pulsation caused by the peristaltic pumps and relying on passive factors such as the inherent resistance to the flow of the liquid etc do not provide any effective pressure dampening. Further, the pressure dampening system may not provide any substantial dampening to the pressure pulsation caused by the physiological contractions of the cavity walls.

Synchronization of the Inflo and the Outflow Pumps

The inflow pump 1 and the out flow pump 20 are both positive displacement pumps and both these pumps could also be housed on a single common driving shaft in a manner that both pumps were synchronized. By synchronization here means that when the inflow pump produces a positive pressure pulse inside the tissue cavity the outflow pump should produce a negative pressure pulse in the cavity. Such synchronization could be achieved by hit and trial empirical means by adjusting the spatial orientation of a piston, related to the inflow pump, with a corresponding peristaltic pump roller in such a manner that the amplitude of the resultant pressure pulse waveform inside the cavity could be made as less as possible. However such a system of synchronization on a common central shaft is not practically easy. Further in such a system if the pressure needs to be varied then the same could be possible only by varying the diameter D of the constriction site 8. Also in such a system the inflow and the out flow pumps cannot be run independently of each other. Thus in such a system it would be mandatory to have a variable dynamic constriction site preferably under the control in a manner as described in this manuscript.

A System of Incorporating Multiple Peristaltic Pump Tubes

In the preceding parts of the manuscript the peristaltic pump 20 is shown to have one single tube 19 which come in contact with the rollers of the peristaltic pumps. Arbitrarily referring to the outflow pump 20, $$R1 = \frac{\pi \times B^2 \times L}{4} \times RPM$$

where R1=Flow rate of pump 20, B=inner diameter of the peristaltic pump tube 4, L=length of tube 4 and RPM=revolution per minute of pump 5. If the value B is doubled then for the same RPM the flow rate R1 doubles. Similarly if L doubles then also for RPM the flow rate R1 doubles. However keeping in mind the mechanical constraints the values B and L cannot exceed a certain practical value. However if two tubes like tube 19 are used in parallel in the pump 20 then the mathematical expression for the flow rate could be written as follows:

$$R1 = \frac{\pi \times B^2 \times L}{4} \times RPM \times 2$$

This implies that if two peristaltic pump tubes are used instead of one single tube then the flow rate becomes double for the same RPM and if three tubes are used then the flow rate becomes three times and so on. The frequency of the 'pressure pulsations' created by a peristaltic pump is directly proportional to the pump RPM. The said 'pressure pulsations' are undesirable thus it is helpful to keep their frequency as minimal as possible if the flow rate is not compromised. Thus this system of incorporating two or more peristaltic pump tubes helps in attaining a higher flow rate for a relatively lesser RPM. It is but obvious that the said two or more than two parallel tubes are connected to each other at the inlet and the outlet ends of the peristaltic pump.

Determination of the Instantaneous Real Time Rate of Fluid Intravasation

Fluid intravasation is a process by which the irrigation fluid enters into the patient's body system and if excess volume of fluid is intravasated it can be dangerous to the patient's life. Thus, keeping in mind surgical safety, it is extremely important to constantly know the rate at which such intravasation occurs so that corrective surgical measures can be taken before a dangerous volume of fluid intravasates. The inventors propose that one fluid flow rate sensor each be incorporated in the inflow tube and the outflow tube. Referring to FIG. 1 the inflow flow rate sensor should be located in the inflow tube 11 anywhere between the inlet port of the endoscope and the outlet end of the fluid source reservoir 10. Such a flow rate sensor would measure the rate at which fluid enters into the tissue cavity 15 and the same is being termed as 'cavity inflow rate'. Obviously the 'cavity inflow rate' is the true inflow rate for the tissue cavity. Similarly the outflow flow rate sensor should be located anywhere in the out flow tube between the outflow port of the endoscope and the inlet end of the outflow peristaltic pump 14 or any other outflow positive displacement pump. However if an additional or optional constriction site housing tube 31 is also connected to the out flow tube 18 as shown in FIG. 4 then the outflow flow rate sensor should be located between the outflow port of the endoscope and the point at which the proximal end of the constriction site housing tube 31 is connected to the outflow tube 18. The outflow flow rate sensor measures the rate at which fluid is extracted from the tissue cavity which is the same as R2 that is the flow rate of the outflow pump. Now the real time rate of fluid intravasation, being termed as R3, can be determining by subtracting R2 from the 'cavity inflow rate', the mathematical expression for the same being can be written as R3=Cavity inflow rate−R2. The said flow rate sensors should be accurate, reliable, easy to install and should not have any movable parts. The inventors suggest that a the said sensor comprise of a heating coil in physical contact with a metal plate for heating the same and a temperature sensor placed in contact with the metal plate, the temperature of the metal plate being a function of the fluid flow rate. The said flow rate sensors are electrically connected with a microcontroller which automatically subtracts R2 from the 'cavity inflow rate' to give the value R3. The value R3 can also be further integrated with respect to time to give the total volume of fluid intravasated over a certain time interval. The said temperature related flow rate sensor could be a 'hot wire anemometer'.

Determination of the Real Time Rate of Fluid Intravasation Without Using Fluid Flow Rate Sensors The tissue cavity pressure P is a function of the RPM of the inflow piston pump (R1), the cavity outflow rate (R2) and the real time rate of intravasation (R3). The value P increases as the value RPM of the inflow pump increases and decreases as R3 and R2 increase. Thus a mathematical expression could be derived which contains P, RPM of the inflow positive displacement pump, R2 and R3. Such a mathematical expression could be fed into a controller and in this manner the value R3, the real time rate of fluid intravasation could be determined.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The proposed invention has obvious use in hysteroscopic surgery, arthroscopic surgery and TURP surgery. The proposed invention can also be utilized for carrying out endoscopic procedures in the brain and the spine. Brain endoscopic surgery also known as neuro endoscopy is a frequently performed life saving procedure. The human brain has got cavities known as the brain ventricles. Many endoscopic procedures are performed by inserting the endoscope into the brain ventricles and many such procedures utilize continuous flow irrigation. Endoscopic surgery of the spine is also a frequently performed and many endoscopic procedures related to the spine utilize continuous flow irrigation. The proposed invention can be useful in other endoscopic procedures also which require continuous flow irrigation. The present invention can be useful in certain non endoscopic procedures also where a tissue cavity needs to be distended by continuous flow irrigation such as gall stone dissolution, balloon thermal ablation of the endometrium, phako emulsification procedure related to the eye ball cavity and vitrectomy procedure related to the eye ball cavity.

The advantage of predicting the required volume for the irrigation fluid at the beginning of the surgery has already been explained. Such maneuver though extremely simple is extremely helpful. In the present invention the outflow rate remains fixed all through the surgery unless intentionally changed by the surgeon. The average total surgical time for similar endoscopic procedures usually does no vary and the surgeons on the basic of their past experience always have an idea of the approximate time which an endoscopic procedure takes. Such time multiplied by the chosen outflow rate R2 gives a fairly accurate idea of the total volume of irrigation which would be consumed in the proposed endoscopic procedure if intravasation was to be ignored and the surgeons again by their past experience also have a fairly rough idea of the of the volume of fluid which is intravasated in a certain duration of time for specific endoscopic procedures. In this manner the total fluid that would be required in a particular endoscopic procedure can be roughly evaluated but even such rough evaluation is helpful as explained in a previous paragraph entitled 'Predicting the total volume of required irrigation fluid'. It is advisable to take a slightly greater volume than that predicted by the method described in this paragraph.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The Invention is Unique

There is no other prior art system in which two positive displacement pumps running simultaneously at fixed RPM's predictably create and maintain any desired fixed pressure inside a tissue cavity, despite unpredictable irregular physiological contractions of the cavity walls, for any precise and fixed outflow rate for unlimited time. Also the concept of 'pressure pulse dampening system', 'pump synchronization' and using more than one peristaltic pump tubes as discussed in the previous paragraph has not been described in any prior art system. Besides these unique features the invention has many other unique features also as already discussed in the previous paragraphs.

The Heart and Soul of the Invention

The constriction site 8 as described in the manuscript is the heart and soul of the invention without which the invention cannot exist.

Advantages of the Proposed Invention

The proposed invention makes endoscopic procedures extremely safe, simple, more accurate and easy to perform. The proposed invention helps the surgeons to perform endoscopic surgeries with greater safety and confidence especially in the initial phase of their learning curve. Also a distending system based on the proposed invention can be used in multiple endoscopic procedures thus reducing the financial burden on the hospital and the patient. The advantages of proposed invention are summarized in the following table 3 along with the corresponding disadvantages of the prior art systems:

TABLE 3

| ADVANTAGES OF THE PRESENT INVENTION: | DISADVANTAGES OF THE PRIOR ART SYSTEMS: |
|---|---|
| It is possible to create and maintain a desired precise tissue cavity pressure for a desired precise fixed outflow rate including a zero outflow rate. | This is not possible in any prior art system. |
| It is possible to reduce the amplitude of the pressure pulsations created by an outflow positive displacement pump to an almost negligible magnitude irrespective of the pump RPM. | This is not possible in any prior art system. |
| It is possible to reduce the frequency of the pressure pulsations created by an outflow positive displacement pump for the same outflow rate. | Such system is not present in any prior art system. |
| A predictably constant any desired fluid pressure can be maintained inside a tissue cavity for indefinite time. | This is not possible in any prior art system. |
| A predictably constant any desired fluid pressure can be maintained inside a tissue cavity for indefinite time despite physiological cavity wall contractions. | This is not possible in any prior art system. |
| A predictably constant clear endoscopic visualization is possible. | This is not possible in any prior art system. |
| It is possible to achieve a predictably stable mechanical distension of the cavity walls. | This is not possible in any prior art system. |
| It is possible to minimize cavity fluid turbulence to almost negligible levels. | This is not possible in any prior art system. |
| The instantaneous real time rate of fluid intravasation into the patient's body is constantly known by using a hot wire anemometer type of a flow rate sensor. | Such feature is not present in any prior art system. |

CONCLUSION

The proposed invention is novel and unique. The invention relates not only to increasing surgical efficiency in certain endoscopic procedures but it also helps in preventing human morbidity and human mortality in many endoscopic procedures. Thus the proposed invention is extremely useful for entire mankind.

We claim:

1. A system for distending body tissue cavities of subjects by continuous flow irrigation during endoscopic procedures, the system comprising:

a collapsible fluid source reservoir containing a non viscous physiologic liquid, said fluid source reservoir being encircled by a bladder cavity, said bladder cavity being connected to an inflow pneumatic positive displacement pump through an air transporting tube, an auxiliary tube having a fixed constriction site coupled to a wall of the air transporting tube disposed between the positive displacement inflow pump and the bladder cavity, a free end of the auxiliary tube opening directly into the atmosphere, the constriction site having a fixed diameter, wherein the auxiliary tube provides a route for air pumped by the positive displacement pump to escape to the atmosphere;

a fluid supply inflow tube connecting the fluid source reservoir to an inflow port for pumping the fluid at a controlled flow rate into the body tissue cavity, the flow rate of the inflow pump being termed as the inflow rate and the rate at which the fluid from the inflow tube enters into the tissue cavity being termed as the cavity inflow rate;

an inflow liquid pressure transducer connected between the fluid source reservoir and the inflow port, the pressure transducer comprising a pressure transducer tube extending from the fluid supply inflow tube, wherein the pressure transducer measures the fluid pressure via a column of liquid or air present in the lumen of the pressure transducer tube; and an outflow port connectable to an inlet end of a variable speed positive displacement outflow pump through an outflow tube for removing the fluid from the cavity at a controlled flow rate, the flow rate of the outflow pump being termed as the cavity outflow rate, an outlet end of the outflow pump being connected to a waste fluid collecting container, wherein the air transporting tube allows a constant cavity pressure in the body tissue cavity and distends the body tissue cavity by continuous flow irrigation during an endoscopic procedure while the inflow positive displacement pump and the outflow positive displacement pump run simultaneously and regardless of the cavity outflow rate, and wherein the air transporting auxiliary tube is releasably provided between the positive displacement pump and the bladder cavity to enable replacement of the tube with another tube having a different diameter at the constriction site to suit the operational need of the endoscopic procedure.

2. The system as claimed in claim 1, wherein a proximal end of the fluid supply inflow tube is connected to the fluid source reservoir and a distal end of the tube is connected to the inflow port.

3. The system as claimed in claim 1, wherein the positive displacement inflow pump is a piston pump.

4. The system as claimed in claim 1, wherein the tube is provided with a clamping means at the constriction site to enable the user to vary the diameter of the tube at the constriction site to suit the operational needs of endoscopic procedures.

5. The system as claimed in claim 1, wherein the diameter of the tube at the constriction site is in the range of 0.001 mm to a maximum value which is less than the overall diameter of the rest of the tube.

6. The system as claimed in claim 1, wherein the diameter of the tube at the constriction site is in the range of 0.01 to 2.5 mm.

7. The system as claimed in claim 1, further comprising an inflow gas pressure transducer located between the inflow pneumatic pump and the bladder cavity, near the outlet end of the inflow pump, for measuring the gas pressure inside the air transporting tube.

8. The system as claimed in claim 1, wherein a proximal end of the outflow tube is connected to the outlet port and a distal end of the outflow tube is connected to an inlet end of the variable speed positive displacement outflow pump.

9. The system as claimed in claim 1, further comprising an outflow pressure transducer connected between a proximal end of the outflow tube and the inlet end of the variable speed positive displacement outflow pump for measuring the pressure in the outflow tube.

10. The system as claimed in claim 1, wherein the variable speed positive displacement outflow pump is selected from the group consisting of peristaltic pump, piston pump, gear pump and diaphragm pump.

11. The system as claimed in claim 10, wherein the variable speed positive displacement outflow pump is a peristaltic pump.

12. The system as claimed in claim 1, wherein the outlet end of the variable speed positive displacement outflow pump is connected to the waste fluid collecting container through a waste fluid carrying tube.

13. The system as claimed in claim 1, further comprising a microcontroller electrically coupled to the inflow liquid pressure transducer and an inflow gas pressure transducer, the inflow positive displacement pump and the outflow pump for regulating the operation of the inflow and the outflow pumps.

14. The system as claimed in claim 13, wherein the tube is provided with an electromechanical device, to enable the micro-controller to vary the diameter of the constriction site.

15. The system as claimed in claim 1, further comprising a housing tube having a variable size constriction site being provided between the outflow tube and the waste fluid reservoir.

16. The system as claimed in claim 15, wherein a proximal end of the housing tube is connected to the outflow tube near the inlet of the outflow pump.

17. The system as claimed in claim 1, further comprising a fluid replenishing tube connected either directly or indirectly to the fluid source reservoir through a replenishment fluid controlling valve for refilling the fluid source reservoir.

18. The system as claimed in claim 17, wherein the fluid replenishing tube is connected directly to the fluid source reservoir or via the fluid supply inflow tube to the fluid source reservoir.

19. The system as claimed in claim 17, wherein an inflow fluid controlling valve is provided on the inflow tube for preventing the fluid from entering into the tissue cavity during fluid replenishment phase.

20. The system as claimed in claim 1, wherein the fluid supply inflow tube, the outflow tube and the waste fluid carrying tube are flexible, disposable and are made of polymeric material.

21. The system as claimed in claim 1 further comprising a fluid inflow rate sensor connected to the inflow tube.

22. The system as claimed in claim 21, wherein the fluid inflow rate sensor is located in a lumen of the inflow fluid supply conduit tube for measuring the cavity inflow rate.

23. The system as claimed in claim 21, further comprising a fluid outflow rate sensor connected between the proximal end of the outflow tube and the inlet end of the variable speed positive displacement outflow pump for measuring the cavity outflow rate.

24. The system as claimed in claim 23, wherein the fluid inflow and outflow rate sensors consist of a heating coil in physical contact with a metal plate for heating the same and a temperature sensor placed in contact with the metal plate for measuring the temperature of the metal plate, the temperature of the metal plate being a function of the fluid flow rate.

25. The system as claimed in claim 23, wherein the fluid outflow rate sensor is a hot wire anemometer.

26. The system as claimed in claim 23, wherein instantaneous real time rate of fluid intravasation is determined by electrically connecting the inflow and outflow fluid flow rate sensors to a micro-controller.

27. The system as claimed in claim 1, further comprising an inflow pressure variation dampening means provided on the inflow side for dampening the pressure variation inside the body tissue cavity caused by the positive displacement inflow pump.

28. The system as claimed in claim 27, wherein the inflow pressure variation dampening means comprises a single outlet syringe mechanism, the piston of the same being coupled synchronously to the positive displacement inflow pump through a coupling means and the single outlet end of the syringe mechanism being connected to the air transporting tube.

29. The system as claimed in claim 1, further comprising an outflow pressure variation dampening means provided on the outflow side for dampening the pressure variation inside the body tissue cavity caused by the positive displacement outflow pump.

30. The system as claimed in claim 29, wherein the outflow pressure variation dampening means comprises a single outlet syringe mechanism, the piston of the same being coupled synchronously to the positive displacement outflow pump through a coupling means and the single outlet end of the syringe mechanism being connected to the outflow tube.

\* \* \* \* \*